United States Patent
Shiver et al.

(10) Patent No.: US 6,534,312 B1
(45) Date of Patent: Mar. 18, 2003

(54) VACCINES COMPRISING SYNTHETIC GENES

(75) Inventors: John W. Shiver, Doylestown, PA (US); Mary Ellen Davies, Norristown, PA (US); Daniel C. Freed, King of Prussia, PA (US); Margaret A. Liu, Rosemont, PA (US); Helen C. Perry, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/340,798

(22) Filed: Jun. 28, 1999

Related U.S. Application Data

(63) Continuation-in-part of application No. 09/342,404, filed on Jun. 28, 1999, now abandoned, which is a continuation of application No. 08/802,368, filed on Feb. 19, 1997, now abandoned, application No. 09/340,798, which is a continuation of application No. 08/877,418, filed on Jun. 17, 1997, now abandoned.

(60) Provisional application No. 60/020,166, filed on Jun. 21, 1996, provisional application No. 60/020,165, filed on Jun. 21, 1996, and provisional application No. 60/012,082, filed on Feb. 22, 1996.

(51) Int. Cl.⁷ ............................ C12N 5/06; C12Q 1/70; C12P 21/04; A61K 39/21; C07H 21/04
(52) U.S. Cl. ............................. 435/339; 435/5; 435/6; 435/69.7; 424/208.1; 536/23.4
(58) Field of Search ................. 435/5, 6, 69.7, 435/339; 424/208.1; 536/23.4

(56) References Cited

U.S. PATENT DOCUMENTS

| 5,786,464 A | 7/1998 | Seed ............................ 536/235 |
| 5,795,737 A | 8/1998 | Seed et al. ................... 435/69.1 |
| 6,114,148 A | 9/2000 | Seed et al. ................... 435/91.1 |

FOREIGN PATENT DOCUMENTS

| EP | 345242 A2 | 12/1989 |
| EP | 565794 A1 | 10/1993 |
| JP | 950007288 | 1/1995 |
| JP | 08198774 | 8/1996 |
| WO | WO 91/09869 | 7/1991 |
| WO | WO 94/16737 | 8/1994 |
| WO | WO 95/20660 | 8/1995 |
| WO | WO 96/09378 | 3/1996 |
| WO | WO 96/21356 | 7/1996 |
| WO | WO 97/11086 | 3/1997 |
| WO | WO 97/31115 | 8/1997 |
| WO | WO 98/12207 | 3/1998 |

OTHER PUBLICATIONS

Andre, Stefanie; et al., Increased Immune Response Elicited by DNA Vaccination with a Synthetic gp120 Sequence with Optimized Codon Usage, 1998, Journal of Virology, pp. 1497–1503.

(List continued on next page.)

*Primary Examiner*—Hankyel T. Park
(74) *Attorney, Agent, or Firm*—Van Dyke & Associates, P.A.

(57) ABSTRACT

Synthetic polynucleotides comprising a DNA sequence encoding a peptide or protein are provided. The DNA sequence of the synthetic polynucleotides comprise codons optimized for expression in a nonhomologous host. The invention is exemplified by synthetic DNA molecules encoding HIV env as well as modifications of HIV env. The codons of the synthetic molecules include the projected host cell's preferred codons. The synthetic molecules provide preferred forms of foreign genetic material. The synthetic molecules may be used as a polynucleotide vaccine which provides immunoprophylaxis against HIV infection through neutralizing antibody and cell-mediated immunity. This invention provides polynucleotides which, when directly introduced into a vertebrate in vivo, including mammals such as primates and humans, induces the expression of encoded proteins within the animal.

12 Claims, 10 Drawing Sheets

OTHER PUBLICATIONS

Figure 1:
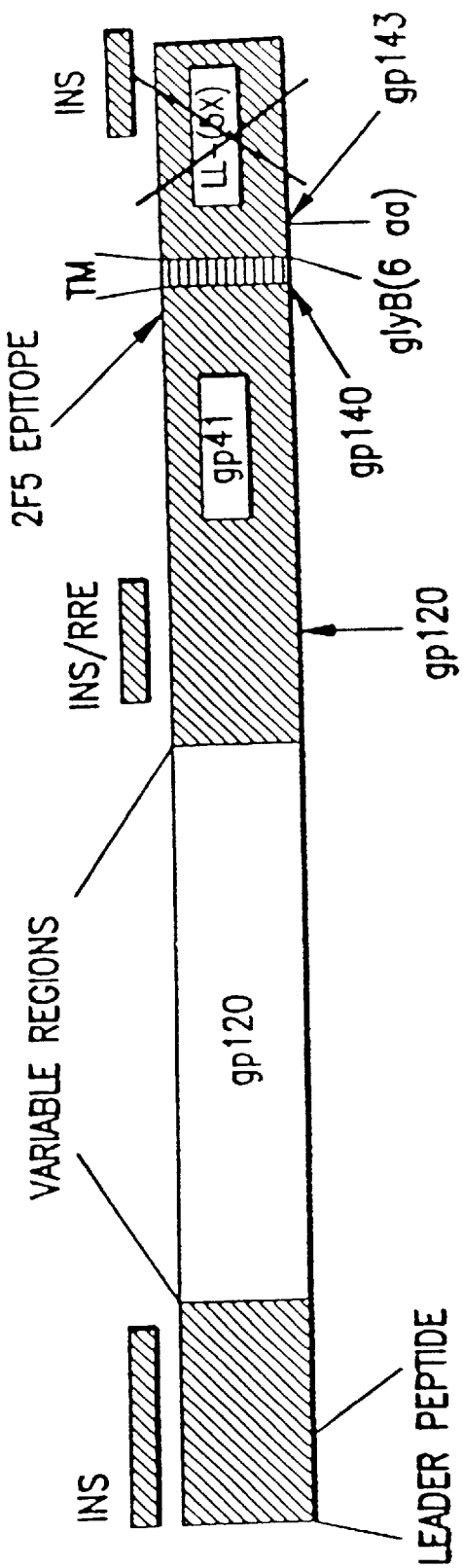
Figure 2:
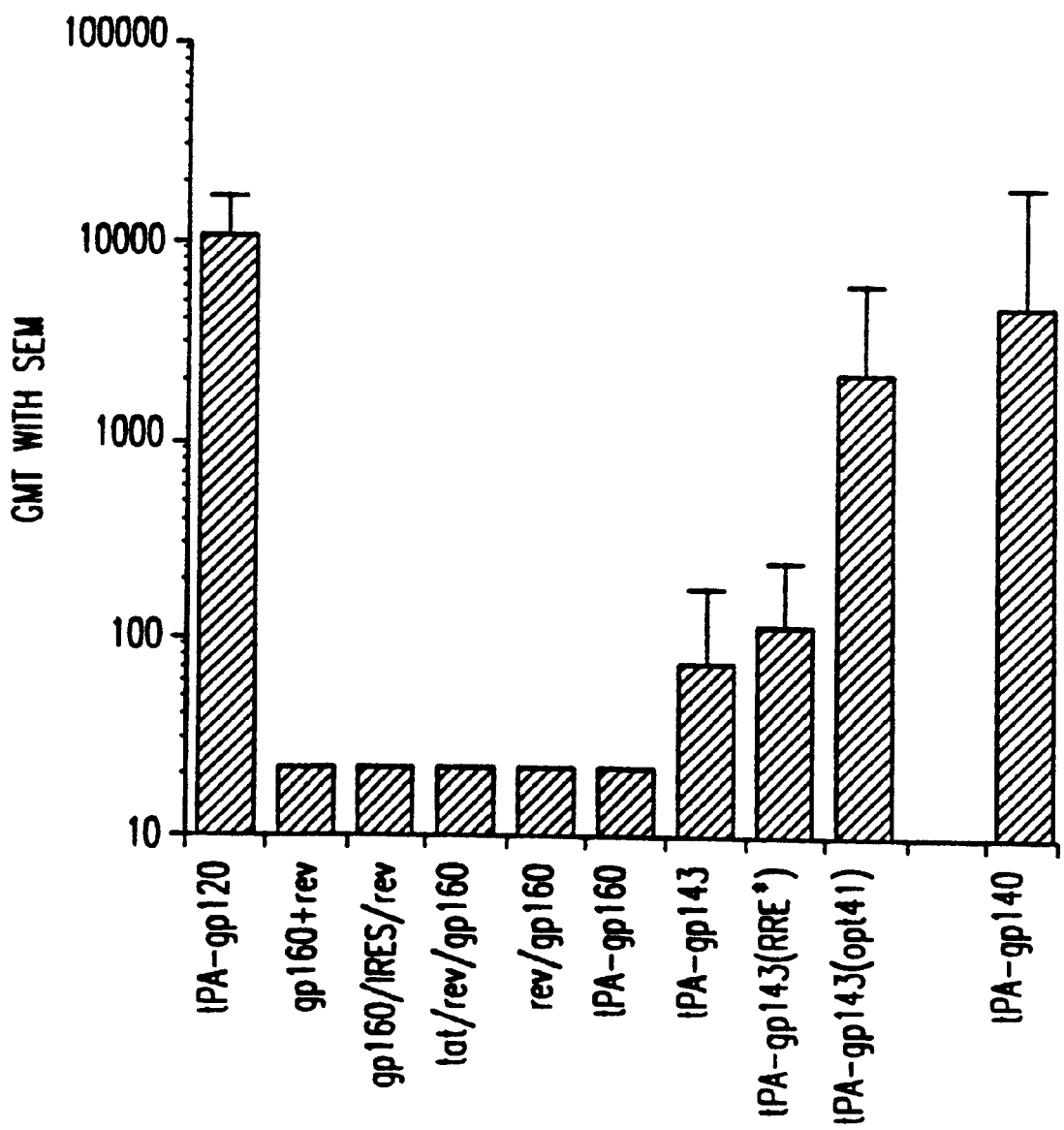
Figure 3:
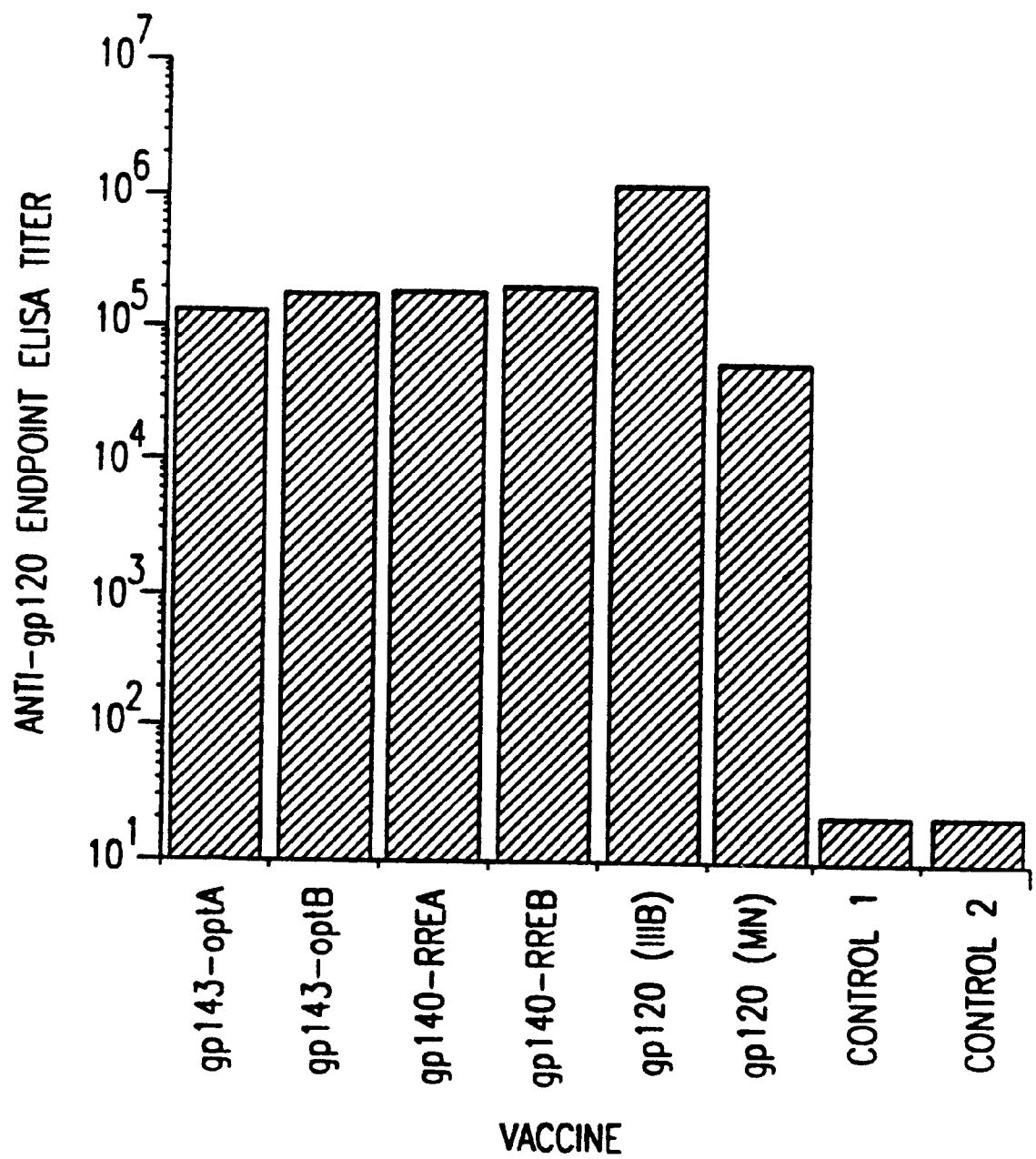
Figure 4:
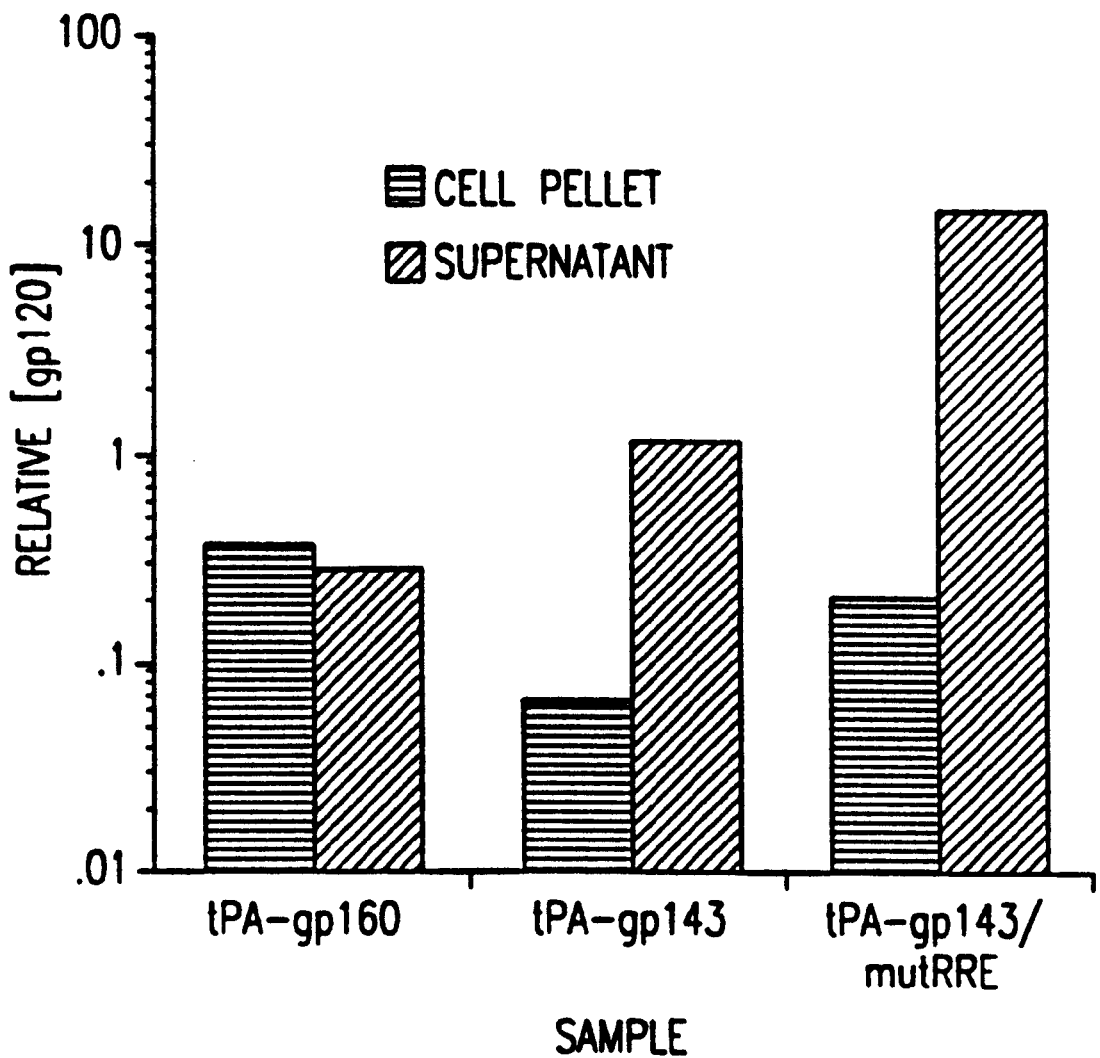
Figure 5:
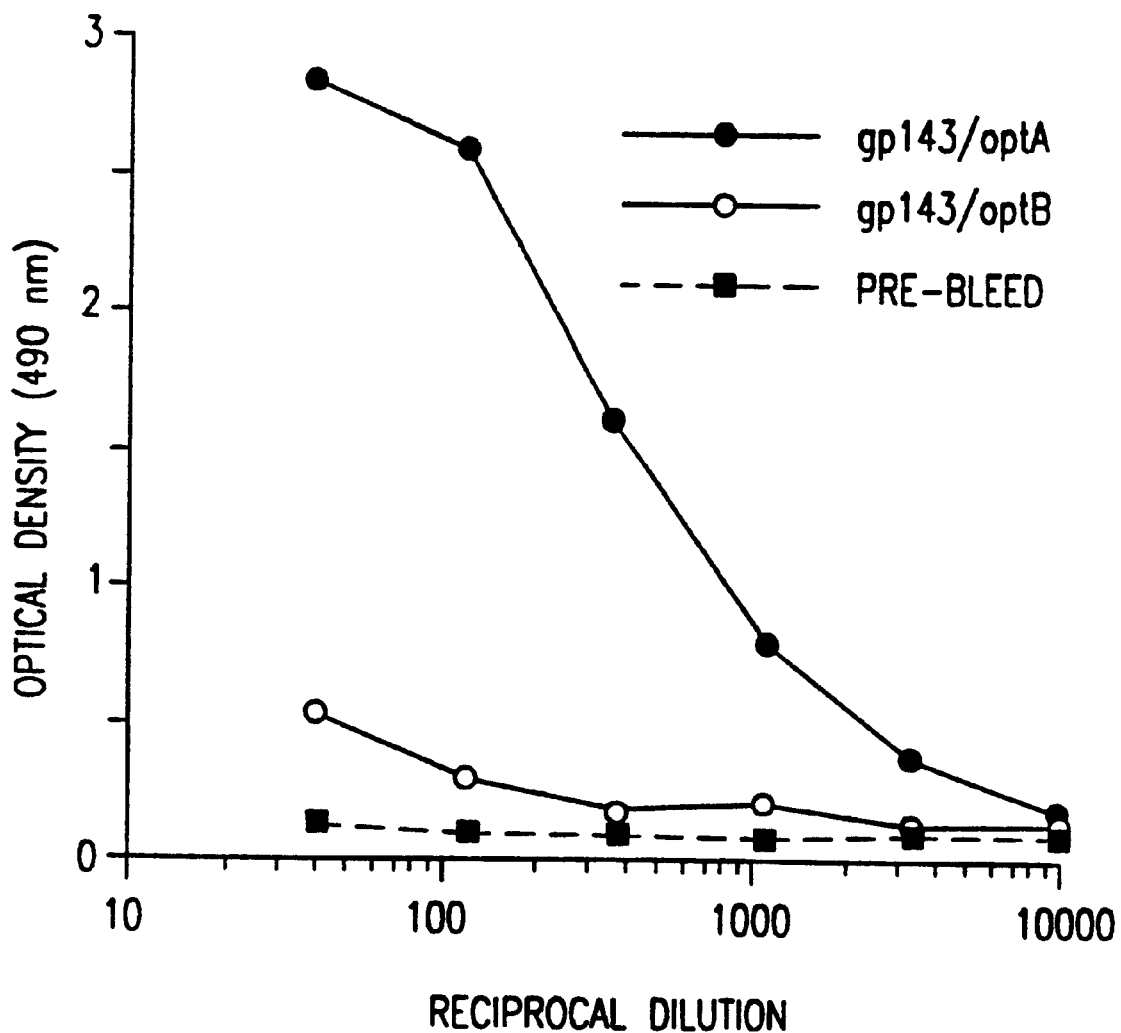
Figure 6:
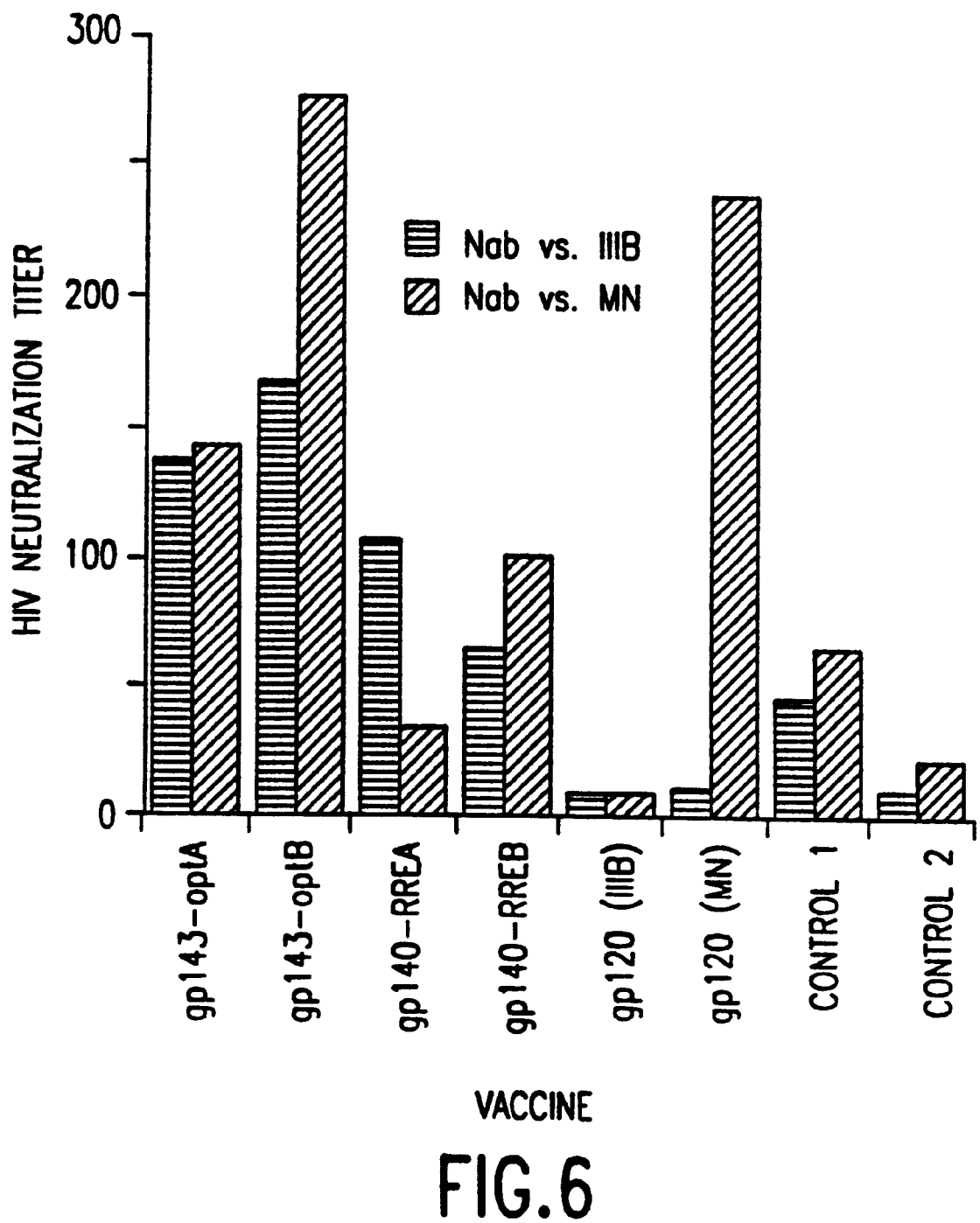
Figure 7:
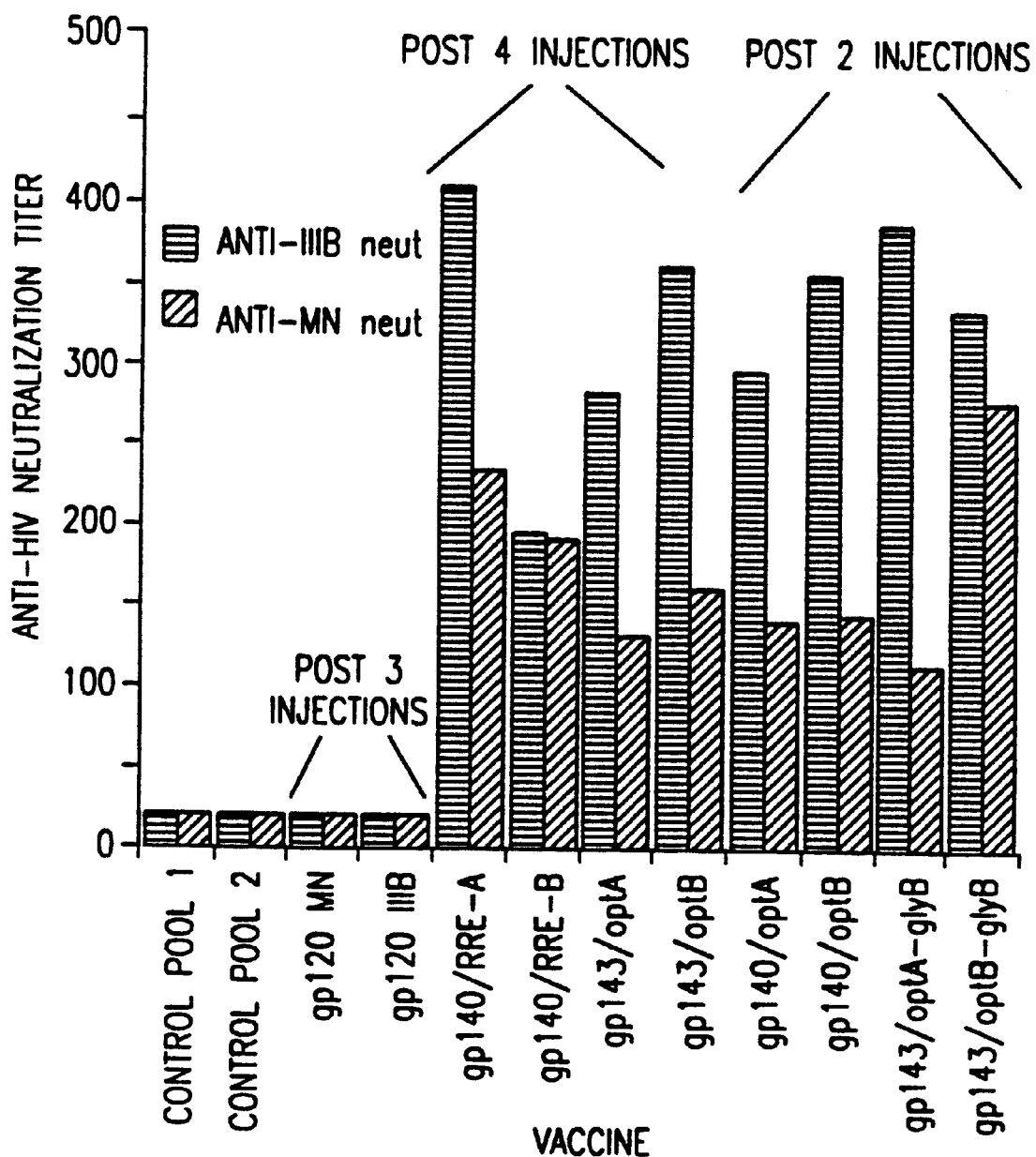

Bagarazzi, M. L.; et al., Nucleic Acid–Based Vaccines as an Approach to Immunization Against Human Immunodeficiency Virus Type–1, 1998, Carr. Top. Microbiol. Immunol.; vol. 226; pp. 107–143.

Belshe, Robert B.; et al., Safty and Immunogenicity of a Fully Glycosylated Recombinant gp160 Human Immunodeficiency Virus Type 1 Vaccine in Subjects at Low Risk of Infection, 1993, Journal of Infectious Diseases; vol. 168; pp. 1387–1395.

Chou, Kuo–Chen and Zhang, Chun–Ting, Diagrammatization of Codon Usage in 339 Human Immunodeficiency Virus Proteins and Its Biological Implication, 1992, Aids Research and Human Retroviruses; vol. 8; No. 12; pp. 1967–1976.

Coney, Leslie; et al., Facilitated DNA inoculation induces anti–HIV–1 immunity in vivo, 1994, Vaccine; vol. 12; No. 16; pp. 1545–1551.

Fahey, J. L. and Schooley, R., Status of immune–based therapies in HIV infection and AIDS, 1992, Clin. Exp. Immunol; vol. 88; pp. 1–5.

Fox, Jeffery L., No winners against AIDS, 1994, Bio/Technology; vol. 12; p. 128.

Fuller, Deborah Heydenburg and Haynes, Joel R., A Qualitative Progression in HIV Type 1 Glycoprotein 120–Specific Cytotoxic Cellular and Humoral Immune Responses in Mice Receiving a DNA–Based Glycoprotein 120 Vaccine, 1994, Aids Researchand Human Retroviruses; vol. 10; No. 11; pp. 1433–1441.

Haas, Jurgen; et al., Codon usage limitation in the expression of HIV–1 envelope glycoprotein, 1996, Current Biology; vol. 6; No. 3; pp. 315–324.

Haynes, Barton F.; et al., Update on the Issues of HIV Vaccine Development, 1996, Ann. Med.; vol. 28; pp. 39–41.

Holler, Tod P.; et al., HIV1 integraseexpressed in *Escherichia coli* from a synthetic gene, 1993, Gene; vol. 136; pp. 323–328.

Lathe, R., Synthetic Oligonucleotide Probes Deduced from Amino Acid Sequence Data—Theoretical and Practical Considerations, 1985, J. Mol. Biol.; vol. 183; pp. 1–12.

Letvin, Norman L.; et al., Potent, protective anti–HIV immune responses generated by bimodal HIV envelope DNA plus protein vaccination, 1997, Proc. Natl. Acad. Sci. USA; vol. 94; pp. 9378–9383.

Liu, Margaret A.; et al., Vaccination of Mice and Nonhuman Primates using HIV–Gene–Containing DNA, 1996, Antibiot. chemother. Basel. Karger; vol. 48; pp. 100–104.

Morikawa, Yuko; Barsov, Eugene; and Jones, Ian, Legitimate and Illegitimate Cleavage of Human Immunodeficiency Virus Glycoproteins by Furin, 1993, Journal of Virology; vol. 67; pp. 3601–3604.

Myers, Gerald; et al., (Edited by), Human Retroviruses and AIDS; A Comilation and Analysis of Nucleic Acid and Amino Acid Sequences, 1990, Published by Theretical Biology and Biophysics Group T–10; pp. 1–A–74 thru 1–A–77.

Okuda, Kenji; et al., Induction of Potent Humoral and Cell–Mediated Immune Responses Following Direct Injection of DNA Encoding the HIV Type 1 env and rev Gene Products, 1995, Aids Research and Human Retroviruses; vol. 11; No. 8; pp. 933–943.

Powell, Michael F.; and Newman, Mark J. (Edited by), Vaccine design; the subunit and adjuvant approach, 1995, Published by Plenum Press, pp. 21, 654.

Rinaldo, Charles; et al., High Levels of Anti–Human Immunodeficiency Virus Type 1 (HIV–1) Memory Cytotoxic T–Lymphocyte Activity and Low Viral Load Are Associated with Lack of Disease in HIV–1–Infected Long–Term Nonprogressors, 1995, Journal of Virology; vol. 69; No. 9; pp. 5838–5842.

Shiver, John; et al., Cytotoxic T Lymphocyte and Helper T Cell Responses foloowing HIV Polynucleotide Vaccination, 1995, Annals New York Academy of Sciences; vol. 772; pp. 198–208.

Wang, Ban; et al., DNA Inoculation Induces Neutralizing Immune Responses Against Human Immunodeficiency Virus Type 1 in Mice and Nonhuman Primates, 1993, DNA and Cell Biology; vol. 9; pp. 799–805.

Wang, Bin; et al., Gene inoculation generates immune responses against human immunodeficiency virus type 1, 1993, Proc. Natl. Acad. Sci. USA; vol. 90; pp. 4156–4160.

Wang, Bin; et al., Vectors and Novel Vaccines; DNA Inoculation Induces Protective in Vivo Immune Responses against Cellular Challenge with HIV–1 Antigen–Expressing Cells, 1994, Aids Research and Human Retroviruses; vol. 10; Supplement 2; pp. S35–S41.

VACCINES COMPRISING SYNTHETIC GENES

CROSS-REFERENCE TO RELATED APPLICATIONS

This application is a continuation of U.S. application Ser. No. 08/877,418, filed Jun. 17, 1997, now abandoned, which claims the benefit of priority of U.S. Provisional Applications, Serial Nos. 60/020,166 and 60/020,165, both filed Jun. 21, 1996. This application also is a continuation in part of U.S. application Ser. No. 09/342,404, filed Jun. 28, 1999, now abandoned which is a continuation of U.S. application Ser. No. 08/802,368, filed Feb. 19, 1997, now abandoned, which claims the benefit of priority of U.S. Provisional Application, Serial No. 60/012,082, filed Feb. 22, 1996. The benefit of priority is claimed to all of the foregoing applications under 35 U.S.C. sections 119 and 120.

BACKGROUND OF THE INVENTION

1. HIV Infection

Human Immunodeficiency Virus-1 (HIV-1) is the etiological agent of acquired human immune deficiency syndrome (AIDS) and related disorders. HIV-1 is an RNA virus of the Retroviridae family and exhibits the 5'LTR-gag-pol-env-LTR3' organization of all retroviruses. In addition, HIV-1 comprises a handful of genes with regulatory or unknown functions, including the tat and rev genes. The env gene encodes the viral envelope glycoprotein that is translated as a 160-kilodalton (kDa) precursor (gp160) and then cleaved by a cellular protease to yield the external 120-kDa envelope glycoprotein (gp120) and the transmembrane 41-kDa envelope glycoprotein (gp41). Gp120 and gp41 remain associated and are displayed on the viral particles and the surface of HIV-infected cells. Gp120 binds to the CD4 receptor present on the surface of helper T-lymphocytes, macrophages and other target cells. After gp120 binds to CD4, gp41 mediates the fusion event responsible for virus entry.

Infection begins when gp120 on the viral particle binds to the CD4 receptor on the surface of T4 lymphocytes or other target cells. The bound virus merges with the target cell and reverse transcribes its RNA genome into the double-stranded DNA of the cell. The viral DNA is incorporated into the genetic material in the cell's nucleus, where the viral DNA directs the production of new viral RNA, viral proteins, and new virus particles. The new particles bud from the target cell membrane and infect other cells.

Destruction of T4 lymphocytes, which are critical to immune defense, is a major cause of the progressive immune dysfunction that is the hallmark of HIV infection. The loss of target cells seriously impairs the body's ability to fight most invaders, but it has a particularly severe impact on the defenses against viruses, fungi, parasites and certain bacteria, including mycobacteria.

HIV-1 kills the cells it infects by replicating, budding from them and damaging the cell membrane. HIV-1 may kill target cells indirectly by means of the viral gp120 that is displayed on an infected cell's surface. Since the CD4 receptor on T cells has a strong affinity for gp120, healthy cells expressing CD4 receptor can bind to gp120 and fuse with infected cells to form a syncytium. A syncytium cannot survive.

HIV-1 can also elicit normal cellular immune defenses against infected cells. With or without the help of antibodies, cytotoxic defensive cells can destroy an infected cell that displays viral proteins on its surface. Finally, free gp120 may circulate in the blood of individuals infected with HIV-1. The free protein may bind to the CD4 receptor of uninfected cells, making them appear to be infected and evoking an immune response.

Infection with HIV-1 is almost always fatal, and at present there are no cures for HIV-1 infection. Effective vaccines for prevention of HIV-1 infection are not yet available. Because of the danger of reversion or infection, live attenuated virus probably cannot be used as a vaccine. Most subunit vaccine approaches have not been successful at preventing HIV infection. Treatments for HIV-1 infection, while prolonging the lives of some infected persons, have serious side effects. There is thus a great need for effective treatments and vaccines to combat this lethal infection.

2. Vaccines

Vaccination is an effective form of disease prevention and has proven successful against several types of viral infection. Determining ways to present HIV-1 antigens to the human immune system in order to evoke protective humoral and cellular immunity, is a difficult task. To date, attempts to generate an effective HIV vaccine have not been successful. In AIDS patients, free virus is present in low levels only. Transmission of HIV-1 is enhanced by cell-to-cell interaction via fusion and syncytia formation. Hence, antibodies generated against free virus or viral subunits are generally ineffective in eliminating virus-infected cells.

Vaccines exploit the body's ability to "remember" an antigen. After first encounters with a given antigen the immune system generates cells that retain an immunological memory of the antigen for an individual's lifetime. Subsequent exposure to the antigen stimulates the immune response and results in elimination or inactivation of the pathogen.

The immune system deals with pathogens in two ways: by humoral and by cell-mediated responses. In the humoral response lymphocytes generate specific antibodies that bind to the antigen thus inactivating the pathogen. The cell-mediated response involves cytotoxic and helper T lymphocytes that specifically attack and destroy infected cells.

Vaccine development with HIV-1 virus presents problems because HIV-1 infects some of the same cells the vaccine needs to activate in the immune system (i.e., T4 lymphocytes). It would be advantageous to develop a vaccine which inactivates HIV before impairment of the immune system occurs. A particularly suitable type of HIV vaccine would generate an anti-HIV immune response which recognizes HIV variants and which works in HIV-positive individuals who are at the beginning of their infection.

A major challenge to the development of vaccines against viruses, particularly those with a high rate of mutation such as the human immunodeficiency virus, against which elicitation of neutralizing and protective immune responses is desirable, is the diversity of the viral envelope proteins among different viral isolates or strains. Because cytotoxic T-lymphocytes (CTLs) in both mice and humans are capable of recognizing epitopes derived from conserved internal viral proteins, and are thought to be important in the immune response against viruses, efforts have been directed towards the development of CTL vaccines capable of providing heterologous protection against different viral strains.

It is known that CD8+ CTLs kill virally-infected cells when their T cell receptors recognize viral peptides associated with MHC class I molecules. The viral peptides are derived from endogenously synthesized viral proteins, regardless of the protein's location or function within the virus. Thus, by recognition of epitopes from conserved viral proteins, CTLs may provide cross-strain protection. Peptides capable of associating with MHC class I for CTL recognition originate from proteins that are present in or pass through the cytoplasm or endoplasmic reticulum. In general, exogenous proteins, which enter the endosomal processing pathway (as in the case of antigens presented by MHC class II molecules), are not effective at generating CD8+ CTL responses.

Most efforts to generate CTL responses have used replicating vectors to produce the protein antigen within the cell or they have focused upon the introduction of peptides into the cytosol. These approaches have limitations that may reduce their utility as vaccines. Retroviral vectors have restrictions on the size and structure of polypeptides that can be expressed as fusion proteins while maintaining the ability of the recombinant virus to replicate, and the effectiveness of vectors such as vaccinia for subsequent immunizations may be compromised by immune responses against the vectors themselves. Also, viral vectors and modified pathogens have inherent risks that may hinder their use in humans. Furthermore, the selection of peptide epitopes to be presented is dependent upon the structure of an individual's MHC antigens and, therefore, peptide vaccines may have limited effectiveness due to the diversity of MHC haplotypes in outbred populations.

3. DNA Vaccines

Benvenisty, N., and Reshef, L. [PNAS 83, 9551–9555, (1986)] showed that CaPO4-precipitated DNA introduced into mice intraperitoneally (i.p.), intravenously (i.v.) or intramuscularly (i.m.) could be expressed. The i.m. injection of DNA expression vectors without $CaCl_2$ treatment in mice resulted in the uptake of DNA by the muscle cells and expression of the protein encoded by the DNA. The plasmids were maintained episomally and did not replicate. Subsequently, persistent expression has been observed after i.m. injection in skeletal muscle of rats, fish and primates, and cardiac muscle of rats. The technique of using nucleic acids as therapeutic agents was reported in WO90/11092 (Oct. 4, 1990), in which naked polynucleotides were used to vaccinate vertebrates.

It is not necessary for the success of the method that immunization be intramuscular. The introduction of gold microprojectiles coated with DNA encoding bovine growth hormone (BGH) into the skin of mice resulted in production of anti-BGH antibodies in the mice. A jet injector has been used to transfect skin, muscle, fat, and mammary tissues of living animals. Various methods for introducing nucleic have been reviewed. Intravenous injection of a DNA:cationic liposome complex in mice was shown by Zhu et al., [Science 261:209–211 (Jul. 9, 1993) to result in systemic expression of a cloned transgene. Ulmer et al., [Science 259:1745–1749, (1993)] reported on the heterologous protection against influenza virus infection by intramuscular injection of DNA encoding influenza virus proteins.

The need for specific therapeutic and prophylactic agents capable of eliciting desired immune responses against pathogens and tumor antigens is met by the instant invention. Of particular importance in this therapeutic approach is the ability to induce T-cell immune responses which can prevent infections or disease caused even by virus strains which are heterologous to the strain from which the antigen gene was obtained. This is of particular concern when dealing with HIV as this virus has been recognized to mutate rapidly and many virulent isolates have been identified [see, for example, LaRosa et al., Science 249:932–935 (1990), identifying 245 separate HIV isolates]. In response to this recognized diversity, researchers have attempted to generate CTLs based on peptide immunization. Thus, Takahashi et al., [Science 255:333–336 (1992)] reported on the induction of broadly cross-reactive cytotoxic T cells recognizing an HIV envelope (gp160) determinant. However, those workers recognized the difficulty in achieving a truly cross-reactive CTL response and suggested that there is a dichotomy between the priming or restimulation of T cells, which is very stringent, and the elicitation of effector function, including cytotoxicity, from already stimulated CTLs.

Wang et al. reported on elicitation of immune responses in mice against HIV by intramuscular inoculation with a cloned, genomic (unspliced) HIV gene. However, the level of immune responses achieved in these studies was very low. In addition, the Wang et al., DNA construct utilized an essentially genomic piece of HIV encoding contiguous Tat/rev-gp160-Tat/rev coding sequences. As is described in detail below, this is a suboptimal system for obtaining high-level expression of the gp160. It also is potentially dangerous because expression of Tat contributes to the progression of Kaposi's Sarcoma.

WO 93/17706 describes a method for vaccinating an animal against a virus, wherein carrier particles were coated with a gene construct and the coated particles are accelerated into cells of an animal. In regard to HIV, essentially the entire genome, minus the long terminal repeats, was proposed to be used. That method represents substantial risks for recipients. It is generally believed that constructs of HIV should contain less than about 50% of the HIV genome to ensure safety of the vaccine; this ensures that enzymatic moieties and viral regulatory proteins, many of which have unknown or poorly understood functions have been eliminated. Thus, a number of problems remain if a useful human HIV vaccine is to emerge from the gene-delivery technology.

The instant invention contemplates any of the known methods for introducing polynucleotides into living tissue to induce expression of proteins. However, this invention provides a novel immunogen for introducing HIV and other proteins into the antigen processing pathway to efficiently generate HIV-specific CTLs and antibodies. The pharmaceutical is effective as a vaccine to induce both cellular and humoral anti-HIV and HIV neutralizing immune responses. In the instant invention, the problems noted above are addressed and solved by the provision of polynucleotide immunogens which, when introduced into an animal, direct the efficient expression of HIV proteins and epitopes without the attendant risks associated with those methods. The immune responses thus generated are effective at recognizing HIV, at inhibiting replication of HIV, at identifying and killing cells infected with HIV, and are cross-reactive against many HIV strains.

4. Codon Usage and Codon Context

The codon pairings of organisms are highly nonrandom, and differ from organism to organism. This information is used to construct and express altered or synthetic genes having desired levels of translational efficiency, to determine which regions in a genome are protein coding regions, to introduce translational pause sites into heterologous genes, and to ascertain relationship or ancestral origin of nucleotide sequences.

The expression of foreign heterologous genes in transformed organisms is now commonplace. A large number of mammalian genes, including, for example, murine and human genes, have been successfully inserted into single celled organisms. Standard techniques in this regard include introduction of the foreign gene to be expressed into a vector such as a plasmid or a phage and utilizing that vector to insert the gene into an organism. The native promoters for such genes are commonly replaced with strong promoters compatible with the host into which the gene is inserted. Protein sequencing machinery permits elucidation of the amino acid sequences of even minute quantities of native protein. From these amino acid sequences, DNA sequences coding for those proteins can be inferred. DNA synthesis is also a rapidly developing art, and synthetic genes corresponding to those inferred DNA sequences can be readily constructed.

Despite the burgeoning knowledge of expression systems and recombinant DNA, significant obstacles remain when one attempts to express a foreign or synthetic gene in an organism. Many native, active proteins, for example, are glycosylated in a manner different from that which occurs when they are expressed in a foreign host. For this reason, eukaryotic hosts such as yeast may be preferred to bacterial hosts for expressing many mammalian genes. The glycosylation problem is the subject of continuing research.

Another problem is more poorly understood. Often translation of a synthetic gene, even when coupled with a strong promoter, proceeds much less efficiently than would be expected. The same is frequently true of exogenous genes foreign to the expression organism. Even when the gene is transcribed in a sufficiently efficient manner that recoverable quantities of the translation product are produced, the protein is often inactive or otherwise different in properties from the native protein.

It is recognized that the latter problem is commonly due to differences in protein folding in various organisms. The solution to this problem has been elusive, and the mechanisms controlling protein folding are poorly understood.

The problems related to translational efficiency are believed to be related to codon context effects. The protein coding regions of genes in all organisms are subject to a wide variety of functional constraints, some of which depend on the requirement for encoding a properly functioning protein, as well as appropriate translational start and stop signals. However, several features of protein coding regions have been discerned which are not readily understood in terms of these constraints. Two important classes of such features are those involving codon usage and codon context.

It is known that codon utilization is highly biased and varies considerably between different organisms. Codon usage patterns have been shown to be related to the relative abundance of tRNA isoacceptors. Genes encoding proteins of high versus low abundance show differences in their codon preferences. The possibility that biases in codon usage alter peptide elongation rates has been widely discussed. While differences in codon use are associated with differences in translation rates, direct effects of codon choice on translation have been difficult to demonstrate. Other proposed constraints on codon usage patterns include maximizing the fidelity of translation and optimizing the kinetic efficiency of protein synthesis.

Apart from the non-random use of codons, considerable evidence has accumulated that codon/anticodon recognition is influenced by sequences outside the codon itself, a phenomenon termed "codon context." There exists a strong influence of nearby nucleotides on the efficiency of suppression of nonsense codons as well as missense codons. Clearly, the abundance of suppressor activity in natural bacterial populations, as well as the use of "termination" codons to encode selenocysteine and phosphoserine require that termination be context-dependent. Similar context effects have been shown to influence the fidelity of translation, as well as the efficiency of translation initiation.

Statistical analyses of protein coding regions of *E. coli* have demonstrate another manifestation of "codon context." The presence of a particular codon at one position strongly influences the frequency of occurrence of certain nucleotides in neighboring codons, and these context constraints differ markedly for genes expressed at high versus low levels. Although the context effect has been recognized, the predictive value of the statistical rules relating to preferred nucleotides adjacent to codons is relatively low. This has limited the utility of such nucleotide preference data for selecting codons to effect desired levels of translational efficiency.

The advent of automated nucleotide sequencing equipment has made available large quantities of sequence data for a wide variety of organisms. Understanding those data presents substantial difficulties. For example, it is important to identify the coding regions of the genome in order to relate the genetic sequence data to protein sequences. In addition, the ancestry of the genome of certain organisms is of substantial interest. It is known that genomes of some organisms are of mixed ancestry. Some sequences that are viral in origin are now stably incorporated into the genome of eukaryotic organisms. The viral sequences themselves may have originated in another substantially unrelated species. An understanding of the ancestry of a gene can be important in drawing proper analogies between related genes and their translation products in other organisms.

There is a need for a better understanding of codon context effects on translation, and for a method for determining the appropriate codons for any desired translational effect. There is also a need for a method for identifying coding regions of the genome from nucleotide sequence data. There is also a need for a method for controlling protein folding and for insuring that a foreign gene will fold appropriately when expressed in a host. Genes altered or constructed in accordance with desired translational efficiencies would be of significant worth.

Another aspect of the practice of recombinant DNA techniques for the expression by microorganisms of proteins of industrial and pharmaceutical interest is the phenomenon of "codon preference". While it was earlier noted that the existing machinery for gene expression is genetically transformed host cells will "operate" to construct a given desired product, levels of expression attained in a microorganism can be subject to wide variation, depending in part on specific alternative forms of the amino acid-specifying genetic code present in an inserted exogenous gene. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist a variable natural hierarchy or "preference" for certain codons in certain types of cells.

As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an E. coli host will depend to some extent on the frequency of codon use. For example, a gene rich in TTA codons will in all probability be poorly expressed in E. coli, whereas a CTG rich gene will probably highly express the polypeptide. Similarly, when yeast cells are the projected transformation host cells for expression of a leucine-rich polypeptide, a preferred codon for use in an inserted DNA would be TTA.

The implications of codon preference phenomena on recombinant DNA techniques are manifest, and the phenomenon may serve to explain many prior failures to achieve high expression levels of exogenous genes in successfully transformed host organisms-a less "preferred" codon may be repeatedly present in the inserted gene and the host cell machinery for expression may not operate as efficiently. This phenomenon suggests that synthetic genes which have been designed to include a projected host cell's preferred codons provide a preferred form of foreign genetic material for practice of recombinant DNA techniques.

5. Protein Trafficking

The diversity of function that typifies eukaryote cells depends upon the structural differentiation of their membrane boundaries. To generate and maintain these structures, proteins must be transported from their site of synthesis in the endoplasmic reticulum to predetermined destinations throughout the cell. This requires that the trafficking proteins display sorting signals that are recognized by the molecular machinery responsible for route selection located at the access points to the main trafficking pathways. Sorting decisions for most proteins need to be made only once as they traverse their biosynthetic pathways since their final destination, the cellular location at which they perform their function, becomes their permanent residence.

Maintenance of intracellular integrity depends in part on the selective sorting and accurate transport of proteins to their correct destinations. Over the past few years the dissection of the molecular machinery for targeting and localization of proteins has been studied vigorously. Defined sequence motifs have been identified on proteins which can act as 'address labels'. A number of sorting signals have been found associated with the cytoplasmic domains of membrane proteins.

SUMMARY OF THE INVENTION

Synthetic polynucleotides comprising a DNA sequence encoding a peptide or protein are provided. The DNA sequence of the synthetic polynucleotides comprise codons optimized for expression in a nonhomologous host. The invention is exemplified by synthetic DNA molecules encoding HIV env as well as modifications of HIV env. The codons of the synthetic molecules include the projected host cell's preferred codons. The synthetic molecules provide preferred forms of foreign genetic material. The synthetic molecules may be used as a polynucleotide vaccine which provides effective immunoprophylaxis against HIV infection through neutralizing antibody and cell-mediated immunity. This invention provides polynucleotides which, when directly introduced into a vertebrate in vivo, including mammals such as primates and humans, induces the expression of encoded proteins within the animal.

BRIEF DESCRIPTION OF THE DRAWINGS

FIG. 1 shows HIV env cassette-based expression strategies.

FIG. 2 shows DNA vaccine mediated anti-gp120 responses.

FIG. 3 shows anti-gp120 ELISA titers of murine DNA vaccinee sera.

FIG. 4 shows the relative expression of gp120 after HIV env PNV cell culture transfection.

FIG. 5 shows the mean anti-gp120 ELISA responses following tPA-gp143/optA vs. optB DNA vaccination.

FIG. 6 shows the neutralization of HIV by murine DNA vaccinee sera.

FIG. 7 shows HIV neutralization by sera from murine HIV env DNA vaccinees.

FIG. 8 is an immunoblot analysis of optimized HIV env DNA constructs.

FIG. 9 shows anti-gp120 ELISA responses in rhesus monkeys following final vaccination with gp140 DNA and o-gp160 protein.

FIG. 10 shows SHIV neutralizing antibody responses of rhesus monkeys following final vaccination.

DETAILED DESCRIPTION OF THE INVENTION

Synthetic polynucleotides comprising a DNA sequence encoding a peptide or protein are provided. The DNA sequence of the synthetic polynucleotides comprise codons optimized for expression in a nonhomologous host. The invention is exemplified by synthetic DNA molecules encoding HIV env as well as modifications of HIV env are provided. The codons of the synthetic molecules include the projected host cell's preferred codons. The synthetic molecules provide preferred forms of foreign genetic material. The synthetic molecules may be used as a polynucleotide vaccine which provides immunoprophylaxis against HIV infection through neutralizing antibody and cell-mediated immunity. This invention provides polynucleotides which, when directly introduced into a vertebrate in vivo, including mammals such as primates and humans, induces the expression of encoded proteins within the animal.

Therefore, synthetic DNA molecules encoding HIV env and synthetic DNA molecules encoding modified forms of HIV env are provided. The codons of the synthetic molecules are designed so as to use the codons preferred by the projected host cell. As noted above, the synthetic molecules of this portion of the invention may be used as a polynucleotide vaccine which provides effective immunoprophylaxis against HIV infection through neutralizing antibody and cell-mediated immunity. The synthetic molecules may be used as an immunogenic composition. This portion of the invention also provides polynucleotides which, when directly introduced into a vertebrate in vivo, including mammals such as primates and humans, induces the expression of encoded proteins within the animal.

As used herein, a polynucleotide is a nucleic acid which contains essential regulatory elements such that upon introduction into a living, vertebrate cell, it is able to direct the cellular machinery to produce translation products encoded by the genes comprising the polynucleotide. In one embodiment of the invention, the polynucleotide is a polydeoxyribonucleic acid comprising at least one HIV gene operatively linked to a transcriptional promoter. In another embodiment of the invention, the polynucleotide vaccine (PNV) comprises polyribonucleic acid encoding at least one HIV gene which is amenable to translation by the eukaryotic cellular machinery (ribosomes, tRNAs, and other translation factors). Where the protein encoded by the polynucleotide is one which does not normally occur in that animal except in pathological conditions, (i.e., a heterologous protein) such as proteins associated with human immunodeficiency virus, (HIV), the etiologic agent of acquired immune deficiency syndrome, (AIDS), the animals' immune system is activated to launch a protective immune response. Because these exogenous proteins are produced by the animals' tissues, the expressed proteins are processed by the major histocompatibility system, MHC, in a fashion analogous to when an actual infection with the related organism (HIV) occurs. The result, as shown in this disclosure, is induction of immune responses against the cognate pathogen.

Accordingly, the instant inventors have prepared nucleic acids which, when introduced into the biological system induce the expression of HIV proteins and epitopes. The induced antibody response is both specific for the expressed HIV protein, and neutralizes HIV. In addition, cytotoxic T-lymphocytes which specifically recognize and destroy HIV infected cells are induced.

The instant invention provides a method for using a polynucleotide which, upon introduction into mammalian tissue, induces the expression in a single cell, in vivo, of discrete gene products. The instant invention provides a different solution which does not require multiple manipulations of rev dependent HIV genes to obtain rev-independent genes. The rev-independent expression system described herein is useful in its own right and is a system for demonstrating the expression in a single cell in vivo of a single desired gene-product.

Because many of the applications of the instant invention apply to anti-viral vaccination, the polynucleotides are frequently referred to as a polynucleotide vaccine, or PNV. This is not to say that additional utilities of these polynucleotides, in immune stimulation and in anti-tumor therapeutics, are considered to be outside the scope of the invention.

In one embodiment of this invention, a gene encoding an HIV gene product is incorporated in an expression vector. The vector contains a transcriptional promoter recognized by an eukaryotic RNA polymerase, and a transcriptional terminator at the end of the HIV gene coding sequence. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator. The combination of CMVintA-BGH terminator is particularly preferred.

To assist in preparation of the polynucleotides in prokaryotic cells, an antibiotic resistance marker is also preferably included in the expression vector under transcriptional control of a prokaryotic promoter so that expression of the antibiotic does not occur in eukaryotic cells. Ampicillin resistance genes, neomycin resistance genes and other pharmaceutically acceptable antibiotic resistance markers may be used. To aid in the high level production of the polynucleotide by fermentation in prokaryotic organisms, it is advantageous for the vector to contain a prokaryotic origin of replication and be of high copy number. A number of commercially available prokaryotic cloning vectors provide these benefits. It is desirable to remove non-essential DNA sequences. It is also desirable that the vectors not be able to replicate in eukaryotic cells. This minimizes the risk of integration of polynucleotide vaccine sequences into the recipients' genome. Tissue-specific promoters or enhancers may be used whenever it is desirable to limit expression of the polynucleotide to a particular tissue type.

In one embodiment, the expression vector pnRSV is used, wherein the Rous Sarcoma Virus (RSV) long terminal repeat (LTR) is used as the promoter. In another embodiment, V1, a mutated pBR322 vector into which the CMV promoter and the BGH transcriptional terminator were cloned is used. In another embodiment, the elements of V1 and pUC19 have been combined to produce an expression vector named V1J. Into V1J or another desirable expression vector is cloned an HIV gene, such as gp120, gp41, gp160, gag, pol, env, or any other HIV gene which can induce anti-HIV immune responses. In another embodiment, the ampicillin resistance gene is removed from V1J and replaced with a neomycin resistance gene, to generate V1J-neo into different HIV genes have been cloned for use according to this invention. In another embodiment, the vector is V1Jns, which is the same as V1Jneo except that a unique Sfi1 restriction site has been engineered into the single Kpn1 site at position 2114 of V1J-neo. The incidence of Sfi1 sites in human genomic DNA is very low (approximately 1 site per 100,000 bases). Thus, this vector allows careful monitoring for expression vector integration into host DNA, simply by Sfi1 digestion of extracted genomic DNA. In a further refinement, the vector is V1R. In this vector, as much non-essential DNA as possible was "trimmed" from the vector to produce a highly compact vector. This vector is a derivative of V1Jns. This vector allows larger inserts to be used, with less concern that undesirable sequences are encoded and optimizes uptake by cells.

One embodiment of this invention incorporates genes encoding HIV gp160, gp120, gag and other gene products from laboratory adapted strains of HIV such as SF2, IIIB or MN. Those skilled in the art will recognize that the use of genes from HIV-2 strains having analogous function to the genes from HIV-1 would be expected to generate immune responses analogous to those described herein for HIV-1 constructs. The cloning and manipulation methods for obtaining these genes are known to those skilled in the art.

It is recognized that elicitation of immune responses against laboratory adapted strains of HIV may not be adequate to provide neutralization of primary field isolates of HIV. Thus, in another embodiment of this invention, genes from virulent, primary field isolates of HIV are incorporated in the polynucleotide immunogen. This is accomplished by preparing cDNA copies of the viral genes and then subcloning the individual genes into the polynucleotide immunogen. Sequences for many genes of many HIV strains are now publicly available on GENBANK and such primary, field isolates of HIV are available from the National Institute of Allergy and Infectious Diseases (NIAID) which has contracted with Quality Biological, Inc., [7581 Lindbergh Drive, Gaithersburg, Md. 20879] to make these strains available. Such strains are also available from the World Health Organization (WHO) [Network for HIV Isolation and Characterization, Vaccine Development Unit, Office of Research, Global Programme on AIDS, CH-1211 Geneva 27, Switzerland]. From this work those skilled in the art will recognize that one of the utilities of the instant invention is to provide a system for in vivo as well as in vitro testing and analysis so that a correlation of HIV sequence diversity with serology of HIV neutralization, as well as other parameters can be made. Incorporation of genes from primary isolates of HIV strains provides an immunogen which induces immune responses against clinical isolates of the virus and thus meets a need as yet unmet in the field. Furthermore, as the virulent isolates change, the immunogen may be modified to reflect new sequences as necessary.

To keep the terminology consistent, the following convention is followed herein for describing polynucleotide immunogen constructs: "Vector name-HIV strain-gene-additional elements". Thus, a construct wherein the gp160 gene of the MN strain is cloned into the expression vector V1Jneo, the name it is given herein is: "V1Jneo-MN-gp160". The additional elements that are added to the construct are described in further detail below. As the etiologic strain of the virus changes, the precise gene which is optimal for incorporation in the pharmaceutical may be changed. However, as is demonstrated below, because CTL responses are induced which are capable of protecting against heterologous strains, the strain variability is less critical in the immunogen and vaccines of this invention, as compared with the whole virus or subunit polypeptide based vaccines. In addition, because the pharmaceutical is easily manipulated to insert a new gene, this is an adjustment which is easily made by the standard techniques of molecular biology.

The term "promoter" as used herein refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers."

The term "leader" as used herein refers to a DNA sequence at the 5' end of a structural gene which is transcribed along with the gene. The leader usually results in the protein having an N-terminal peptide extension sometimes called a pro-sequence. For proteins destined for either secretion to the extracellular medium or a membrane, this signal sequence, which is generally hydrophobic, directs the protein into endoplasmic reticulum from which it is discharged to the appropriate destination.

The term "intron" as used herein refers to a section of DNA occurring in the middle of a gene which does not code for an amino acid in the gene product. The precursor RNA of the intron is excised and is therefore not transcribed into mRNA nor translated into protein.

The term "cassette" refers to the sequence of the present invention which contains the nucleic acid sequence which is to be expressed. The cassette is similar in concept to a cassette tape. Each cassette will have its own sequence. Thus by interchanging the cassette the vector will express a different sequence. Because of the restrictions sites at the 5' and 3' ends, the cassette can be easily inserted, removed or replaced with another cassette.

The term "3' untranslated region" or "3' UTR" refers to the sequence at the 3' end of a structural gene which is usually transcribed with the gene. This 3' UTR region usually contains the poly A sequence. Although the 3' UTR is transcribed from the DNA it is excised before translation into the protein.

The term "Non-Coding Region" or "NCR" refers to the region which is contiguous to the 3' UTR region of the structural gene. The NCR region contains a transcriptional termination signal.

The term "restriction site" refers to a sequence specific cleavage site of restriction endonucleases.

The term "vector" refers to some means by which DNA fragments can be introduced into a host organism or host tissue. There are various types of vectors including plasmid, bacteriophages and cosmids.

The term "effective amount" means sufficient PNV is injected to produce the adequate levels of the polypeptide. One skilled in the art recognizes that this level may vary.

To provide a description of the instant invention, the following background on HIV is provided. The human immunodeficiency virus has a ribonucleic acid (RNA) genome. This RNA genome must be reverse transcribed according to methods known in the art in order to produce a cDNA copy for cloning and manipulation according to the methods taught herein. At each end of the genome is a long terminal repeat which acts as a promoter. Between these termini, the genome encodes, in various reading frames, gag-pol-env as the major gene products: gag is the group specific antigen; pol is the reverse transcriptase, or polymerase; also encoded by this region, in an alternate reading frame, is the viral protease which is responsible for post-translational processing, for example, of gp160 into gp120 and gp41; env is the envelope protein; vif is the virion infectivity factor; rev is the regulator of virion protein expression; neg is the negative regulatory factor; vpu is the virion productivity factor "u"; tat is the trans-activator of transcription; vpr is the viral protein r. The function of each of these elements has been described.

In one embodiment of this invention, a gene encoding an HIV or SIV protein is directly linked to a transcriptional promoter. The env gene encodes a large, membrane bound protein, gp160, which is post-translationally modified to gp41 and gp120. The gp120 gene may be placed under the control of the cytomegalovirus promoter for expression. However, gp120 is not membrane bound and therefore, upon expression, it may be secreted from the cell. As HIV tends to remain dormant in infected cells, it is desirable that immune responses directed at cell-bound HIV epitopes also be generated. Additionally, it is desirable that a vaccine produce membrane bound, oligomeric ENV antigen similar in structure to that produced by viral infection in order to generate the most efficacious antibody responses for viral neutralization. This goal is accomplished herein by expression in vivo of a secreted gp140 epitope (gp140>gp120+ ectodomain of gp41) or the cell-membrane associated epitope, gp160, to prime the immune system. However, expression of gp160 is repressed in the absence of rev due to non-export from the nucleus of non-spliced genes. For an understanding of this system, the life cycle of HIV must be described in further detail.

In the life cycle of HIV, upon infection of a host cell, HIV RNA genome is reverse-transcribed into a proviral DNA which integrates into host genomic DNA as a single transcriptional unit. The LTR provides the promoter which transcribes HIV genes from the 5' to 3' direction (gag, pol, env), to form an unspliced transcript of the entire genome. The unspliced transcript functions as the mRNA from which gag and pol are translated, while limited splicing must occur for translation of env encoded genes. For the regulatory gene product rev to be expressed, more than one splicing event must occur because in the genomic setting, rev and env overlap. In order for transcription of env to occur, rev transcription must stop, and vice versa. In addition, the presence of rev is required for export of unspliced RNA from the nucleus. For rev to function in this manner, however, a rev responsive element (RRE) must be present on the transcript [Malim et al., Nature 338:254–257 (1989)].

In the polynucleotide vaccine of this invention, the obligatory splicing of certain HIV genes is eliminated by providing fully spliced genes (i.e.: the provision of a complete open reading frame for the desired gene product without the need for switches in the reading frame or elimination of noncoding regions; those of ordinary skill in the art would recognize that when splicing a particular gene, there is some latitude in the precise sequence that results; however so long as a functional coding sequence is obtained, this is acceptable). Thus, in one embodiment, the entire coding sequence for gp160 is spliced such that no intermittent expression of each gene product is required.

The dual humoral and cellular immune responses generated according to this invention are particularly significant to inhibiting HIV infection, given the propensity of HIV to mutate within the population, as well as in infected individuals. In order to formulate an effective protective vaccine for HIV it is desirable to generate both a multivalent antibody response for example to gp160 (env is approximately 80% conserved across various HIV-1, lade B strains, which are the prevalent strains in US human populations), the principal neutralization target on HIV, as well as cytotoxic T cells reactive to the conserved portions of gp160 and, internal viral proteins encoded by gag. We have made an HIV vaccine comprising gp160 genes selected from common laboratory strains; from predominant, primary viral isolates found within the infected population; from mutated gp160s designed to unmask cross-strain, neutralizing antibody epitopes; and from other representative HIV genes such as the gag and pol genes (~95% conserved across HIV isolates.

Virtually all HIV seropositive patients who have not advanced towards an inimunodeficient state harbor anti-gag CTLs while about 60% of these patients show cross-strain, gp160-specific CTLs. The amount of HIV specific CTLs found in infected individuals that have progressed on to the disease state known as AIDS, however, is much lower, demonstrating the significance of our findings that we can induce cross-strain CTL responses.

Immune responses induced by our env and gag polynucleotide vaccine constructs are demonstrated in mice and primates. Monitoring antibody production to env in mice allows confirmation that a given construct is suitably immunogenic, i.e., a high proportion of vaccinated animals show an antibody response. Mice also provide the most facile animal model suitable for testing CTL induction by our constructs and are therefore used to evaluate whether a particular construct is able to generate such activity. Monkeys (African green, rhesus, chimpanzees) provide additional species including primates for antibody evaluation in larger, non-rodent animals. These species are also preferred to mice for antisera neutralization assays due to high levels of endogenous neutralizing activities against retroviruses observed in mouse sera. These data demonstrate that sufficient immunogenicity is engendered by our vaccines to achieve protection in experiments in a chimpanzee/HIV$_{IIIB}$ challenge model based upon known protective levels of neutralizing antibodies for this system. However, the currently emerging and increasingly accepted definition of protection in the scientific community is moving away from so-called "sterilizing immunity", which indicates complete protection from HIV infection, to prevention of disease. A number of correlates of this goal include reduced blood viral titer, as measured either by HIV reverse transcriptase activity, by infectivity of samples of serum, by ELISA assay of p24 or other HIV antigen concentration in blood, increased CD4+ T-cell concentration, and by extended survival rates [see, for example, Cohen, J., Science 262:1820–1821, 1993, for a discussion of the evolving definition of anti-HIV vaccine efficacy]. The immunogens of the instant invention also generate neutralizing immune responses against infectious (clinical, primary field) isolates of HIV.

Immunology
A. Antibody Responses to env.
1. gp160 and gp120

An ELISA assay is used to determine whether vaccine vectors expressing either secreted gp120 or membrane-bound gp160 are efficacious for production of env-specific antibodies. Initial in vitro characterization of env expression by our vaccination vectors is provided by immunoblot analysis of gp160 transfected cell lysates. These data confirm and quantitate gp160 expression using anti-gp41 and anti-gp120 monoclonal antibodies to visualize transfectant cell gp160 expression. In one embodiment of this invention, gp160 is preferred to gp120 for the following reasons: (1) an initial gp120 vector gave inconsistent immunogenicity in mice and was very poorly or non-responsive in African green Monkeys; (2) gp160 contributes additional neutralizing antibody as well as CTL epitopes by providing the addition of approximately 190 amino acid residues due to the inclusion of gp41; (3) gp160 expression is more similar to viral env with respect to tetramer assembly and overall conformation, which may provide oligomer-dependent neutralization epitopes; and (4) we find that, like the success of membrane-bound, influenza HA constricts for producing neutralizing antibody responses in mice, ferrets, and non-human primates [see Ulmer et al., Science 259:1745–1749, 1993; Montgomery, D., et al., *DNA and Cell Biol.* 12:777–783, 1993] anti-gp160 antibody generation is superior to anti-gp120 antibody generation. Selection of which type of env, or whether a cocktail of env subfragments, is preferred is determined by the experiments outlined below.

2. Presence and Breadth of Neutralizing Activity

ELISA positive antisera from monkeys is tested and shown to neutralize both homologous and heterologous HIV strains.

3. V3 vs. Non-V3 Neutralizing Antibodies

A major goal for env PNVs is to generate broadly neutralizing antibodies. It has now been shown that antibodies directed against V3 loops are very strain specific, and the serology of this response has been used to define strains.

a. Non-V3 neutralizing antibodies appear to primarily recognize discontinuous, structural epitopes within gp120 which are responsible for CD4 binding. Antibodies to this domain are polyclonal and more broadly cross-neutralizing probably due to restraints on mutations imposed by the need for the virus to bind its cellular ligand. An in vitro assay is used to test for blocking gp120 binding to CD4 immobilized on 96 well plates by sera from immunized animals. A second in vitro assay detects direct antibody binding to synthetic peptides representing selected V3 domains immobilized on plastic. These assays are compatible for antisera from any of the animal types used in our studies and define the types of neutralizing antibodies our vaccines have generated as well as provide an in vitro correlate to virus neutralization.

b. gp41 harbors at least one major neutralization determinant, corresponding to the highly conserved linear epitope recognized by the broadly neutralizing 2F5 monoclonal antibody (commercially available from Viral Testing Systems Corp., Texas Commerce Tower, 600 Travis Street, Suite 4750, Houston, Tex. 77002-3005(USA), or Waldheim Pharmazeutika GmbH, Boltzmangasse 11, A1091 Wien, Austria), as well as other potential sites including the well-conserved "fusion peptide" domain located at the N-terminus of gp41. Besides the detection of antibodies directed against gp41 by immunoblot as described above, an in vitro assay test is used for antibodies which bind to synthetic peptides representing these domains immobilized on plastic.

4. Maturation of the Antibody Response

In HIV seropositive patients, the neutralizing antibody responses progress from chiefly anti-V3 to include more broadly neutralizing antibodies comprising the structural gp120 domain epitopes described above (#3), including gp41 epitopes. These types of antibody responses are monitored over the course of both time and subsequent vaccinations.

B. T Cell Reactivities Against env and gag.

1. Generation of CTL Responses

Viral proteins which are synthesized within cells give rise to MHC I-restricted CTL responses. Each of these proteins elicits CTL in seropositive patients. Our vaccines also are able to elicit CTL in mice. The immunogenetics of mouse strains are conducive to such studies, as demonstrated with influenza NP, [see Ulmer et al., Science 259:1745–1749, 1993]. Several epitopes have been defined for the HIV proteins env, rev, nef and gag in Balb/c mice, thus facilitating in vitro CTL culture and cytotoxicity assays. It is advantageous to use syngeneic tumor lines, such as the murine mastocytoma P815, transfected with these genes to provide targets for CTL as well as for in vitro antigen specific restimulation. Methods for defining immunogens capable of eliciting MHC class I-restricted cytotoxic T lymphocytes are known [see Calin-Laurens, et al., *Vaccine* 11(9):974–978, 1993; see particularly Eriksson, et al., *Vaccine* 11(8):859–865, 1993, wherein T-cell activating epitopes on the HIV gp120 were mapped in primates and several regions, including gp120 amino acids 142–192, 296–343, 367–400, and 410–453 were each found to induce lymphoproliferation; furthermore, discrete regions 248–269 and 270–295 were lymphoproliferative. A peptide encompassing amino acids 152–176 was also found to induce HIV neutralizing antibodies], and these methods may be used to identify immunogenic epitopes for inclusion in the PNV of this invention. Alternatively, the entire gene encoding gp160, gp120, protease, or gag could be used. For additional review on this subject, see for example, Shirai et al., *J. Immunol* 148:1657–1667, 1992; Choppin et al., *J. Immunol* 147:569–574, 1991; Choppin et al., *J. Immunol* 147:575–583, 1991; Berzofsky et al., *J. Clin. Invest.* 88:876–884, 1991. As used herein, T-cell effector function is associated with mature T-cell phenotype, for example, cytotoxicity, cytokine secretion for B-cell activation, and/or recruitment or stimulation of macrophages and neutrophils.

2. Measurement of $T_H$ Activities

Spleen cell cultures derived from vaccinated animals are tested for recall to specific antigens by addition of either recombinant protein or peptide epitopes. Activation of T cells by such antigens, presented by accompanying splenic antigen presenting cells, APCs, is monitored by proliferation of these cultures or by cytokine production. The pattern of cytokine production also allows classification of $T_H$ response as type 1 or type 2. Because dominant $T_H 2$ responses appear to correlate with the exclusion of cellular immunity in immunocompromised seropositive patients, it is possible to define the type of response engendered by a given PNV in patients, permitting manipulation of the resulting immune responses.

3. Delayed Type Hypersensitivity (DTH)

DTH to viral antigen after i.d. injection is indicative of cellular, primarily MHC II-restricted, immunity. Because of the commercial availability of recombinant HIV proteins and synthetic peptides for known epitopes, DTH responses are easily determined in vaccinated vertebrates using these reagents, thus providing an additional in vivo correlate for inducing cellular immunity.

Protection

Based upon the above immunologic studies, it is predictable that our vaccines are effective in vertebrates against challenge by virulent HIV. These studies are accomplished in an $HIV_{IIIB}$/chimpanzee challenge model after sufficient vaccination of these animals with a PNV construct, or a cocktail of PNV constructs comprised of $gp160_{IIIB}$, $gag_{IIIB}$, $nef_{IIIB}$ and $REV_{IIIB}$. The IIIB strain is useful in this regard as the chimpanzee titer of lethal doses of this strain has been established. However, the same studies are envisioned using any strain of HIV and the epitopes specific to or heterologous to the given strain. A second vaccination/challenge model, in addition to chimpanzees, is the scid-hu PBL mouse. This model allows testing of the human lymphocyte immune system and our vaccine with subsequent HIV challenge in a mouse host. This system is advantageous as it is easily adapted to use with any HIV strain and it provides evidence of protection against multiple strains of primary field isolates of HIV. A third challenge model utilizes hybrid HIV/SIV viruses (SHIV), some of which have been shown to infect rhesus monkeys and lead to immunodeficiency disease resulting in death [see Li, J., et al., *J. AIDS* 5:639–646, 1992]. Vaccination of rhesus with our polynucleotide vaccine constructs is protective against subsequent challenge with lethal doses of SHIV.

PNV Construct Summary

HIV and other genes are ligated into an expression vector which has been optimized for polynucleotide vaccinations. Essentially all extraneous DNA is removed, leaving the essential elements of transcriptional promoter, immunogenic epitopes, transcriptional terminator, bacterial origin of replication and antibiotic resistance gene.

Expression of HIV late genes such as env and gag is rev-dependent and requires that the rev response element (RRE) be present on the viral gene transcript. A secreted form of gp120 can be generated in the absence of rev by substitution of the gp120 leader peptide with a heterologous leader such as from tPA (tissue-type plasminogen activator), and preferably by a leader peptide such as is found in highly expressed mammalian proteins such as immunoglobulin leader peptides. We have inserted a tPA-gp120 chimeric gene into V1Jns which efficiently expresses secreted gp120 in transfected cells (RD, a human rhabdomyosarcoma line). Monocistronic gp160 does not produce any protein upon transfection without the addition of a rev expression vector.

Representative Construct Components Include (but are not restricted to):

1. tPA-$gp120_{MN}$;
2. $gp160_{IIIB}$;
3. $gag_{IIIB}$: for anti-gag CTL;
4. tPA-$gp120_{IIIB}$;
5. tPA-gp140
6. tPA-gp160 with structural mutations: V1, V2, and/or V3 loop deletions or substitutions
7. Genes encoding antigens expressed by pathogens other than HIV, such as, but not limited to, influenza virus nucleoprotein, hemagglutinin, matrix, neurarininidase, and other antigenic proteins; herpes simplex virus genes; human papillomavirus genes; tuberculosis antigens; hepatitis A, B, or C virus antigens.

The protective efficacy of polynucleotide HIV immunogens against subsequent viral challenge is demonstrated by immunization with the non-replicating plasmid DNA of this invention. This is advantageous since no infectious agent is involved, assembly of virus particles is not required, and determinant selection is permitted. Furthermore, because the sequence of gag and protease and several of the other viral gene products is conserved among various strains of HIV, protection against subsequent challenge by a virulent strain of HIV that is homologous to, as well as strains heterologous to the strain from which the cloned gene is obtained, is enabled.

The i.m. injection of a DNA expression vector encoding a gp160 results in the generation of significant protective immunity against subsequent viral challenge. In particular, gp160-specific antibodies and primary CTLs are produced. Immune responses directed against conserved proteins can be effective despite the antigenic shift and drift of the variable envelope proteins. Because each of the HIV gene products exhibit some degree of conservation, and because CTL are generated in response to intracellular expression and MHC processing, it is predictable that many virus genes give rise to responses analogous to that achieved for gp160. Thus, many of these genes have been cloned, as shown by the cloned and sequenced junctions in the expression vector (see below) such that these constructs are immunogenic agents in available form.

The invention offers a means to induce cross-strain protective immunity without the need for self-replicating agents or adjuvants. In addition, immunization with the instant polynucleotides offers a number of other advantages. This approach to vaccination should be applicable to tumors as well as infectious agents, since the $CD8^+$ CTL response is important for both pathophysiological processes [K. Tanaka et al., Annu. Rev. Immunol. 6, 359 (1988)]. Therefore, eliciting an immune response against a protein crucial to the transformation process may be an effective means of cancer protection or immunotherapy. The generation of high titer antibodies against expressed proteins after injection of viral protein and human growth hormone DNA suggests that this is a facile and highly effective means of making antibody-based vaccines, either separately or in combination with cytotoxic T-lymphocyte vaccines targeted towards conserved antigens.

The ease of producing and purifying DNA constructs compares favorably with traditional methods of protein purification, thus facilitating the generation of combination vaccines. Accordingly, multiple constructs, for example encoding gp160, gp120, gp41, or any other HIV gene may be prepared, mixed and co-administered. Because protein expression is maintained following DNA injection, the persistence of B- and T-cell memory may be enhanced, thereby engendering long-lived humoral and cell-mediated immunity.

Standard techniques of molecular biology for preparing and purifying DNA constructs enable the preparation of the DNA immunogens of this invention. While standard techniques of molecular biology are therefore sufficient for the production of the products of this invention, the specific constructs disclosed herein provide novel polynucleotide immunogens which surprisingly produce cross-strain and primary HIV isolate neutralization, a result heretofore unattainable with standard inactivated whole virus or subunit protein vaccines.

The amount of expressible DNA or transcribed RNA to be introduced into a vaccine recipient will depend on the strength of the transcriptional and.translational promoters used and on the immunogenicity of the expressed gene product. In general, an immunologically or prophylactically effective dose of about 1 ng to 100 mg, and preferably about 10 $\mu$g to 300 $\mu$g is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided. Following vaccination with HIV polynucleotide immunogen, boosting with HIV protein immunogens such as gp160, gp120, and gag gene products is also contemplated. Parenteral administration, such as intravenous, intramuscular, subcutaneous or other means of administration of interleukin-12 protein or GM-CSF or similar proteins alone or in combination, concurrently with or subsequent to parenteral introduction of the PNV of this invention is also advantageous.

The polynucleotide may be naked, that is, unassociated with any proteins, adjuvants or other agents which impact on the recipients' immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

The following examples are offered by way of illustration and are not intended to limit the invention in any manner.

EXAMPLE 1

Materials Descriptions

Vectors pF411 and pF412: These vectors were subcloned from vector pSP62 which was constructed in R. Gallo's lab. pSP62 is an available reagent from Biotech Research Laboratories, Inc. pSP62 has a 12.5 kb XbaI fragment of the HXB2 genome subcloned from lambda HXB2. SalI and Xba I digestion of pSP62 yields to HXB2 fragments: 5'-XbaI/SalI, 6.5 kb and 3'-SalI/XbaI, 6 kb. These inserts were subcloned into pUC 18 at SmaI and SalI sites yielding pF411 (5'-XbaI/SalI) and pF412 (3'-XbaI/SalI). pF411 contains gag/pol and pF412 contains tat/rev/env/nef.

Repligen reagents:

recombinant rev (IIIB), #RP1024-10 rec. gp120 (IIIB), #RP1001-10 anti-rev monoclonal antibody, #RP1029-10 anti-gp120 mAB, #1C1, #RP1010-10

AIDS Research and Reference Reagent Program anti-gp41 mAB hybridoma, Chessie 8, #526

The strategies are designed to induce both cytotoxic T lymphocyte (CTL) and neutralizing antibody responses to HIV, principally directed at the HIV gag (~95% conserved) and env (gp160 or gp120; 70–80% conserved) gene products. gp160 contains the only known neutralizing antibody epitopes on the HIV particle while the importance of anti-env and anti-gag CTL responses are highlighted by the known association of the onset of these cellular immunities with clearance of primary viremia following infection, which occurs prior to the appearance of neutralizing antibodies, as well as a role for CTL in maintaining disease-free status. Because HIV is notorious for its genetic diversity, we hope to obtain greater breadth of neutralizing antibodies by including several representative env genes derived from clinical isolates and gp41 (~90% conserved), while the highly conserved gag gene should generate broad cross-strain CTL responses.

EXAMPLE 2
Heterologous Expression of HIV Late Gene Products

HIV structural genes such as env and gag require expression of the HIV regulatory gene, rev, in order to efficiently produce full-length proteins. We have found that rev-dependent expression of gag yielded low levels of protein and that rev itself may be toxic to cells. Although we achieved relatively high levels of rev-dependent expression of gp160 in vitro this vaccine elicited low levels of antibodies to gp160 following in vivo immunization with rev/gp160 DNA. This may result from known cytotoxic effects of rev as well as increased difficulty in obtaining rev function in myotubules containing hundreds of nuclei (rev protein needs to be in the same nucleus as a rev-dependent transcript for gag or env protein expression to occur). However, it has been possible to obtain rev-independent expression using selected modifications of the env gene. Evaluation of these plasmids for vaccine purposes is underway.

In general, our vaccines have utilized primarily HIV (IIIB) env and gag genes for optimization of expression within our generalized vaccination vector, V1Jns, which is comprised of a CMV immediate-early (IE) promoter, BGH polyadenylation site, and a pUC backbone. Varying efficiencies, depending upon how large a gene segment is used (e.g., gp120 vs. gp160), of rev-independent expression may be achieved for env by replacing its native secretory leader peptide with that from the tissue-specific plasminogen activator (tPA) gene and expressing the resulting chimeric gene behind the CMVIE promoter with the CMV intron A. tPA-gp120 is an example of a secreted gp120 vector constructed in this fashion which functions well enough to elicit anti-gp120 immune responses in vaccinated mice and monkeys.

Because of reports that membrane-anchored proteins may induce much more substantial (and perhaps more specific for HIV neutralization) antibody responses compared to secreted proteins as well as to gain additional immune epitopes, we prepared V1Jns-tPA-gp160 and V1Jns-rev/gp160. The tPA-gp160 vector produced detectable quantities of gp160 and gp120, without the addition of rev, as shown by immunoblot analysis of transfected cells, although levels of expression were much lower than that obtained for rev/gp160, a rev-dependent gp160-expressing plasmid. This is probably because inhibitory regions (designated INS), which confer rev dependence upon the gp160 transcript, occur at multiple sites within gp160 including at the COOH-terminus of gp41 (see FIG. 1 for schematic view of gp143 construct strategies). A vector was prepared for a COOH-terminally truncated form of tPA-gp160, tPA-gp143, which was designed to increase the overall expression levels of env by elimination of these inhibitory sequences. The gp143 vector also eliminates intracellular gp41 regions containing peptide motifs (such as leu-leu) known to cause diversion of membrane proteins to the lysosomes rather than the cell surface. Thus, gp143 may be expected to increase both expression of the env protein (by decreasing rev-dependence) and the efficiency of transport of protein to the cell surface compared to full-length gp160 where these proteins may be better able to elicit anti-gp160 antibodies following DNA vaccination. tPA-gp143 was further modified by extensive silent mutagenesis of the rev response element (RRE) sequence (350 bp) to eliminate additional inhibitory sequences for expression. This construct, gp143/mutRRE, was prepared in two forms: either eliminating (form A) or retaining (form B) proteolytic cleavage sites for gp120/41. Both forms were prepared because of literature reports that vaccination of mice using uncleavable gp160 expressed in vaccinia elicited much higher levels of antibodies to gp160 than did cleavable forms.

A quantitative ELISA for gp160/gp120 expression in cell transfectants was developed to determine the relative expression capabilities for these vectors. In vitro transfection of 293 cells followed by quantification of cell-associated vs. secreted/released gp120 yielded the following results: (1) tPA-gp160 expressed 5–10× less gp120 than rev/gp160 with similar proportions retained intracellularly vs. trafficked to the cell surface; (2) tPA-gp143 gave 3–6× greater secretion of gp120 than rev/gp160 with only low levels of cell-associated gp143, confirming that the cytoplasmic tail of gp160 causes intracellular retention of gp160 which can be overcome by partial deletion of this sequence; and, (3) tPA-gp143/mutRRE A and B gave ~10× greater expression levels of protein than did parental tPA-gp143 while elimination of proteolytic processing was confirmed for form A. FIG. 4 presents representative data supporting points (1)–(3).

Thus, our strategy to increase rev-independent expression has yielded stepwise increases in overall expression as well as redirecting membrane-anchored gp143 to the cell surface away from lysosomes. It is important to note that it should be possible to insert gp120 sequences derived from various viral isolates within a vector cassette containing these modifications which reside either at the $NH_2$-terminus (tPA leader) or COOH-terminus (gp41), where few antigenic differences exist between different viral strains. In other words, this is a generic construct which can easily be modified by inserting gp120 derived from various primary viral isolates to obtain clinically relevant vaccines.

To apply these expression strategies to viruses that are relevant for vaccine purposes and confirm the generality of our approaches, we also prepared a tPA-gp120 vector derived from a primary HIV isolate (containing the North American consensus V3 peptide loop; macrophage-tropic and nonsyncytia-inducing phenotypes). This vector gave high expression/secretion of gp120 with transfected 293 cells and elicited anti-gp120 antibodies in mice demonstrating that it was cloned in a functional form. Primary isolate gp160 genes will also be used for expression in the same way as for gp160 derived from laboratory strains.

EXAMPLE 3

Immune Responses to HIV-1 env Polynucleotide Vaccines

African green (AGM) and Rhesus (RHM) monkeys which received gp120 DNA vaccines showed low levels of neutralizing antibodies following 2–3 vaccinations, which could not be increased by additional vaccination. These results, as well as increasing awareness within the HIV vaccine field that oligomeric gp160 is probably a more relevant target antigen for eliciting neutralizing antibodies than gp120 monomers (Moore and Ho, *J. Virol.* 67: 863 (1993)), have led us to focus upon obtaining effective expression of gp160-based vectors (see above). Mice and AGM were also vaccinated with the primary isolate derived tPA-gp120 vaccine. These animals exhibited anti-V3 peptide (using homologous sequence) reciprocal endpoint antibody titers ranging from 500–5000, demonstrating that this vaccine design is functional for clinically relevant viral isolates.

The gp160-based vaccines, rev-gp160 and tPA-gp160, failed to consistently elicit antibody responses in mice and nonhuman primates or yielded low antibody titers. Our initial results with the tPA-gp143 plasmid yielded geometric mean titers>$10^3$ in mice and AGM following two vaccinations. These data indicate that we have significantly improved the immunogenicity of gp160-like vaccines by increasing expression levels. This construct, as well as the tPA-gp143/mutRRE A and B vectors, will continue to be characterized for antibody responses, especially for virus neutralization.

Significantly, gp120 DNA vaccination produced potent helper T cell responses in all lymphatic compartments tested (spleen, blood, inguinal, mesenteric, and iliac nodes) with $T_H1$-like cytokine secretion profiles (i.e., g-interferon and IL-2 production with little or no IL-4). These cytokines generally promote strong cellular immunity and have been associated with maintenance of a disease-free state for HIV-seropositive patients. Lymph nodes have been shown to be primary sites for HIV replication, harboring large reservoirs of virus even when virus cannot be readily detected in the blood. A vaccine which can elicit anti-HIV immune responses at a variety of lymph sites, such as we have shown with our DNA vaccine, may help prevent successful colonization of the lymphatics following initial infection.

As stated previously, we consider realization of the following objectives to be essential to maximize our chances for success with this program: (1) env-based vectors capable of generating stronger neutralizing antibody responses in primates; (2) gag and env vectors which elicit strong T-lymphocyte responses as characterized by CTL and helper effector functions in primates; (3) use of env and gag genes from clinically relevant HIV-1 strains in our vaccines and characterization of the immunologic responses, especially neutralization of primary isolates, they elicit; (4) demonstration of protection in an animal challenge model such as chimpahzee/HIV (IIIB) or rhesus/SHIV using appropriate optimized vaccines; and, (5) determination of the duration of immune responses appropriate to clinical use. Significant progress has been made on the first three of these objectives and experiments are in progress to determine whether our recent vaccination constructs for gp160 and gag will improve upon these initial results.

EXAMPLE 4
Vectors For Vaccine Production
A. V1Jneo Expression Vector SEQ. ID 1

It was necessary to remove the $amp^r$ gene used for antibiotic selection of bacteria harboring V1J because ampicillin may not be used in large-scale fermenters. The $amp^r$ gene from the pUC backbone of V1J was removed by digestion with SspI and Eam1105I restriction enzymes. The remaining plasmid was purified by agarose gel electrophoresis, blunt-ended with T4 DNA polymerase, and then treated with calf intestinal alkaline phosphatase. The commercially available $kan^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the $kan^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. We arbitrarily selected V1Jneo#3, referred to as V1Jneo hereafter (SEQ ID:1), which contains the $kan^r$ gene in the same orientation as the $amp^r$ gene in V1J as the expression construct.
B. V1Jns Expression Vector An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).
C. V1Jns-tPA In order to provide an heterologous leader peptide sequence to secreted and/or membrane proteins, V1Jn was modified to include the human tissue-specific plasminogen activator (tPA) leader. Two synthetic complementary oligomers were annealed and then ligated into V1Jn which had been BglII digested. The sense and antisense oligomers were 5'-GATC ACC ATG GAT GCA ATG AAG AGA GGG CTC TGC TGT GTG CTG CTG CTG TGT GGA GCA GTC TTC GTT TCG CCC AGC GA-3' (SEQ.ID:2), and 5'-GAT CTC GCT GGG CGA AAC GAA GAC TGC TCC ACA CAG CAG CAG CAC ACA GCA GAG CCC TCT CTT CAT TGC ATC CAT GGT-3' (SEQ. ID:3). The Kozak sequence is underlined in the sense oligomer. These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing. Additionally, in order to conform with our consensus optimized vector V1Jns (=V1Jneo with an SfiI site), an SfiI restriction site was placed at the KpnI site within the BGH terminator region of V1Jn-tPA by blunting the KpnI site with T4 DNA polymerase followed by ligation with an SfiI linker (catalogue #1138, New England Biolabs). This modification was verified by restriction digestion and agarose gel electrophoresis.

EXAMPLE 5
I. HIV env Vaccine Constructs
Vaccines Producing Secreted env-derived Antigen (gp120 and gp140):

Expression of the rev-dependent env gene as gp120 was conducted as follows: gp120 was PCR-cloned from the MN strain of HIV with either the native leader peptide sequence (V1Jns-gp120), or as a fusion with the tissue-plasminogen activator (tPA) leader peptide replacing the native leader peptide (V1Jns-tPA-gp120). tPA-gp120 expression has been shown to be rev-independent [B. S. Chapman et al., Nuc. Acids Res. 19, 3979 (1991); it should be noted that other leader sequences would provide a similar function in rendering the gp120 gene rev independent]. This was accomplished by preparing the following gp120 constructs utilizing the above described vectors.

EXAMPLE 6
gp120 Vaccine Constructs
A. V1Jns-tPA-HIV$_{MN}$ gp120:

HIV$_{MN}$ gp120 gene (Medimmune) was PCR amplified using oligomers designed to remove the first 30 amino acids of the peptide leader sequence and to facilitate cloning into V1Jns-tPA creating a chimeric protein consisting of the tPA leader peptide followed by the remaining gp120 sequence following amino acid residue 30. This design allows for rev-independent gp120 expression and secretion of soluble gp120 from cells harboring this plasmid. The sense and antisense PCR oligomers used were 5'-CCC CGG ATC CTG ATC ACA GAA AAA TTG TGGGTC ACA GTC-3' (SEQ. ID:4), and 5'-C CCC AGG AATC CAC CTG TTA GCG CTT TTC TCT CTG CAC CAC TCT TCT C-3' (SEQ. ID:5). The translation stop codon is underlined. These oligomers contain BamHI restriction enzyme sites at either end of the translation open reading frame with a BclI site located 3' to the BamHI of the sense oligomer. The PCR product was sequentially digested with BclI followed by BamHI and ligated into V1Jns-tPA which had been BglII digested followed by calf intestinal alkaline phosphatase treatment. The resulting vector was sequenced to confirm in-frame fusion between the tPA leader and gp120 coding sequence, and gp120 expression and secretion was verified by immunoblot analysis of transfected RB cells.

B. V1Jns-tPA-HIV$_{IIIB}$ gp120

This vector is analogous to I.A. except that the HIV IIIB strain was used for gp120 sequence. The sense and antisense PCR oligomers used were: 5'-GGT ACA TGA TCA CA GAA AAA TTG TGG GTC ACA GTC-3' (SEQ.ID:6), and 5'-CCA CAT TGA TCA GAT ATC TTA TCT TTT TTC TCT CTG CAC CAC TCT TC-3' (SEQ.ID:7), respectively. These oligomers provide BclI sites at either end of the insert as well as an EcoRV just upstream of the BclI site at the 3'-end. The 5'-terminal BclI site allows ligation into the BglII site of V1Jns-tPA to create a chimeric tPA-gp120 gene encoding the tPA leader sequence and gp120 without its native leader sequence. Ligation products were verified by restriction digestion and DNA sequencing.

EXAMPLE 7 gp140 Vaccine Constructs

These constructs was prepared by PCR similarly as tPA-gp120 with the tPA leader in place of the native leader, but designed to produce secreted antigen by terminating the gene immediately $NH_2$-terminal of the transmembrane peptide (projected carboxyterminal amino acid sequence=$NH_2$-... TNWLWYIK-COOH) [SEQ.ID:8]. Unlike the gp120-producing constructs, gp140 constructs should produce oligomeric antigen and retain known gp41-contained antibody neutralization epitopes such as ELDKWA (SEQ.ID:53) defined by the 2F5 monoclonal antibody.

Constructs were prepared in two forms (A or B) depending upon whether the gp160 proteolytic cleavage sites at the junction of gp120 and gp41 were retained (B) or eliminated (A) by appropriate amino acid substitutions as described by Kieny et al., (Prot. Eng. 2: 219–255 (1988)) (wild type sequence=$NH_2$-. . .KAKRRVVQREKR. . .COOH (SEQ.ID:9) and the mutated sequence=$NH_2$-. . .KA <u>Q</u><u>N</u><u>H</u>VVQ<u>N</u>E<u>H</u><u>Q</u>. . .COOH (SEQ.ID:10) with mutated amino acids underlined).

A. V1Jns-tPA-gp140/mutRRE-A/SRV-1 3'-UTR (based on HIV-1$_{IIIB}$)

This construct was obtained by PCR using the following sense and antisense PCR oligomers: 5'-CT GAA AGA CCA GCA ACT CCT AGG GAAT TTG GGG TTG CTC TGG-3' (SEQ.ID:11) :, and 5'-CGC AGG GGA GGT GGT CTA GAT ATC TTA TTA TTT TAT ATA CCA CAG CCA ATT TGT TAT G-3' (SEQ ID:12) to obtain an AvrII/EcoRV segment from vector IVB (containing the optimized RRE-A segment). The 3'-UTR, prepared as a synthetic gene segment, that is derived from the Simian Retrovirus-1 (SRV-1, see below) was inserted into an SrfI restriction enzyme site introduced immediately 3'- of the gp140 open reading frame. This UTR sequence has been described previously as facilitating rev-independent expression of HIV env and gag.

B. V1Jns-tPA-gp140/mutRRE-B/SRV-1 3'-UTR (based on HIV-1$_{IIIB}$)

This construct is similar to IIA except that the env proteolytic cleavage sites have been retained by using construct IVC as starting material.

C. V1Jns-tPA-gp140/opt30-A (based on HIV-1$_{IIIB}$)

This construct was derived from IVB by AvrII and SrfI restriction enzyme digestion followed by ligation of a synthetic DNA segment corresponding to gp30 but comprised of optimal codons for translation (see gp32-opt below). The gp30-opt DNA was obtained from gp32-opt by PCR amplification using the following sense and anti-sense oligomers: 5'-GGT ACA CCT AGG CAT CTG GGG CTG CTC TGG-3', (SEQ ID:13) and, 5'-CCA CAT GAT ATC G CCC GGG C TTA TTA TTT GAT GTA CCA CAG CCA GTT GGT GAT G-3', (SEQ ID:14), respectively. This DNA segment was digested with AvrII and EcoRV restriction enzymes and ligated into V1Jns-tPA-gp143/opt32-A (IVD) that had been digested with AvrII and SrfI to remove the corresponding DNA segment. The resulting products were verified by DNA sequencing of ligation junctions and immunoblot analysis.

D. V1Jns-tPA-gp140/opt30-B (based on HIV-1$_{IIIB}$)

This construct is similar to IIC except that the env proteolytic cleavage sites have been retained.

E. V1Jns-tPA-gp140/opt all-A

The env gene of this construct is comprised completely of optimal codons. The constant regions (C1, C5, gp32) are those described in IVB,D,H with an additional synthetic DNA segment corresponding to variable regions 1–5 is inserted using a synthetic DNA segment comprised of optimal codons for translation (see example below based on HIV-1 MN V1–V5).

F. V1Jns-tPA-gp140/opt all-B

This construct is similar to IIE except that the env proteolytic cleavage sites have been retained.

G. V1Jns-tPA-gp140/opt all-A (non-IIIB strains)

This construct is similar to IIE above except that env amino acid sequences from strains other than IIIB are used to determine optimum codon usage throughout the variable (V1–V5) regions.

H. V1Jns-tPA-gp140/opt all-B (non-IIIB strains)

This construct is similar to IIG except that the env proteolytic cleavage sites have been retained.

EXAMPLE 8 gp160 Vaccine Constructs

Constructs were prepared in two forms (A or B) depending upon whether the gp160 proteolytic cleavage sites as described above.

A. V1Jns-rev/env

This vector is a variation of the one described in section D above except that the entire tat coding region in exon 1 is deleted up to the beginning of the rev open reading frame. V1Jns-gp160$_{IIIB}$ (see section A. above) was digested with PstI and KpnI restriction enzymes to remove the 5'-region of the gp160 gene. PCR amplification was used to obtain a DNA segment encoding the first REV exon up to the KpnI site in gp160 from the HXB2 genomic clone. The sense and antisense PCR oligomers were 5'-GGT ACA CTG CAG TCA CCG TCC T ATG GCA GGA AGA AGC GGA GAC-3' (SEQ.ID:15) and 5'-CCA CAT CA GGT ACC CCA TAA TAG ACT GTG ACC-3' (SEQ.ID:16) respectively. These oligomers provide PstI and KpnI restriction enzyme sites at the 5'- and 3'-termini of the DNA fragment, respectively. The resulting DNA was digested with PstI and KpnI, purified from an agarose electrophoretic gel, and ligated with V1Jns-gp160(PstI/KpnI). The resulting plasmid was verified by restriction enzyme digestion.

B. V1Jns-gp160

HIV$_{IIIb}$ gp160 was cloned by PCR amplification from plasmid pF412 which contains the 3'-terminal half of the HIV$_{IIIb}$ genome derived from HIV$_{IIIb}$ clone HXB2. The PCR sense and antisense oligomers were 5'-GGT ACA TGA TCA <u>ACC ATG</u> AGA GTG AAG GAG AAA TAT CAG C-3' (SEQ. ID:17), and 5'-CCA CAT TGA TCA GAT ATC CCC ATC <u>TTA</u> TAG CAA AAT CCT TTC C-3' (SEQ. ID:18), respectively. The Kozak sequence and translation stop codon are underlined. These oligomers provide BclI restriction enzyme sites outside of the translation open reading frame at both ends of the env gene. (BclI-digested sites are compatible for ligation with BglII-digested sites with subsequent loss of sensitivity to both restriction enzymes. BclI was chosen for PCR-cloning gp160 because this gene contains internal BglII and as well as BamHI sites). The antisense oligomer also inserts an EcoRV site just prior to the BclI site as described above for other PCR-derived genes. The amplified gp160 gene was agarose gel-purified, digested with BclI, and ligated to V1Jns which had been digested with BglII and treated with calf intestinal alkaline phosphatase. The cloned gene was about 2.6 kb in size and each junction of gp160 with V1Jns was confirmed by DNA sequencing.

C. V1Jns-tPA-gp160 (based on HIV-1$_{IIIB}$)

This vector is similar to Example 1(C) above, except that the full-length gp160, without the native leader sequence, was obtained by PCR. The sense oligomer was the same as used in I.C. and the antisense oligomer was 5'-CCA CAT TGA TCA GAT ATC CCC ATC TTA TAG CAA AAT CCT TTC C-3' (SEQ.ID:19). These oligomers provide BclI sites at either end of the insert as well as an EcoRV just upstream of the BclI site at the 3'-end. The 5'-terminal BclI site allows ligation into the BglII site of V1Jns-tPA to create a chimeric tPA-gp160 gene encoding the tPA leader sequence and gp160 without its native leader sequence. Ligation products were verified by restriction digestion and DNA sequencing.

D. V1Jns-tPA-gp160/opt C1/opt41-A (based on HIV-1$_{IIIB}$)

This construct was based on IVH, having a complete optimized codon segment for C5 and gp41, rather than gp32, with an additional optimized codon segment (see below) replacing C1 at the amino terminus of gp120 following the tPA leader. The new C1 segment was joined to the remaining gp143 segment via SOE PCR using the following oligomers for PCR to synthesize the joined C1/143 segment: 5'-CCT GTG TGT GAG TTT AAA C TGC ACT GAT TTG AAG AAT GAT ACT AAT AC-3' (SEQ ID:20). The resulting gp143 gene contains optimal codon usage except for V1–V5 regions and has a unique PmeI restriction enzyme site placed at the junction of C1 and V1 for insertion of variable regions from other HIV genes.

E. V1Jns-tPA-gp160/opt C1/opt41-B (Based on HIV-1$_{IIIB}$):

This construct is similar to IIID except that the env proteolytic cleavage sites have been retained.

F V1Jns-tPA-gp160/opt all-A (Based on HIV-1$_{IIIB}$)

The env gene of this construct is comprised completely of optimal codons as described above. The constant regions (C1, C5, gp32) are those described in IIID,E which is used as a cassette (employed for all completely optimized gp160s) while the variable regions, V1–V5, are derived from a synthetic DNA segment comprised of optimal codons.

G. V1Jns-tPA-gp160/opt all-B

This construct is similar to IIIF except that the env proteolytic cleavage sites have been retained.

H. V1Jns-tPA-gp160/opt all-A (Non-IIIB Strains)

This construct is similar to IIIF above except that env amino acid sequences from strains other than IIIB were used to determine optimum codon useage throughout the variable (V1–V5) regions.

I. V1Jns-tPA-gp160/opt all-B (Non-IIIB Strains)

This construct is similar to IIIH except that the env proteolytic cleavage sites have been retained.

EXAMPLE 9 gp143 Vaccine Constructs

These constructs were prepared by PCR similarly as other tPA-containing constructs described above (tPA-gp120, tPA-gp140, and tPA-gp160), with the tPA leader in place of the native leader, but designed to produce COOH-terminated, membrane-bound env (projected intracellular amino acid sequence=NH$_2$-NRVRQGYSP-COOH). This construct was designed with the purpose of combining the increased expression of env accompanying tPA introduction and minimizing the possibility that a transcript or peptide region corresponding to the intracellular portion of env might negatively impact expression or protein stability/transport to the cell surface. Constructs were prepared in two forms (A or B) depending upon whether the gp160 proteolytic cleavage sites were removed or retained as described above. The residual gp41 fragment resulting from truncation to gp143 is referred to as gp32.

A. V1Jns-tPA-gp143

Figure 8:
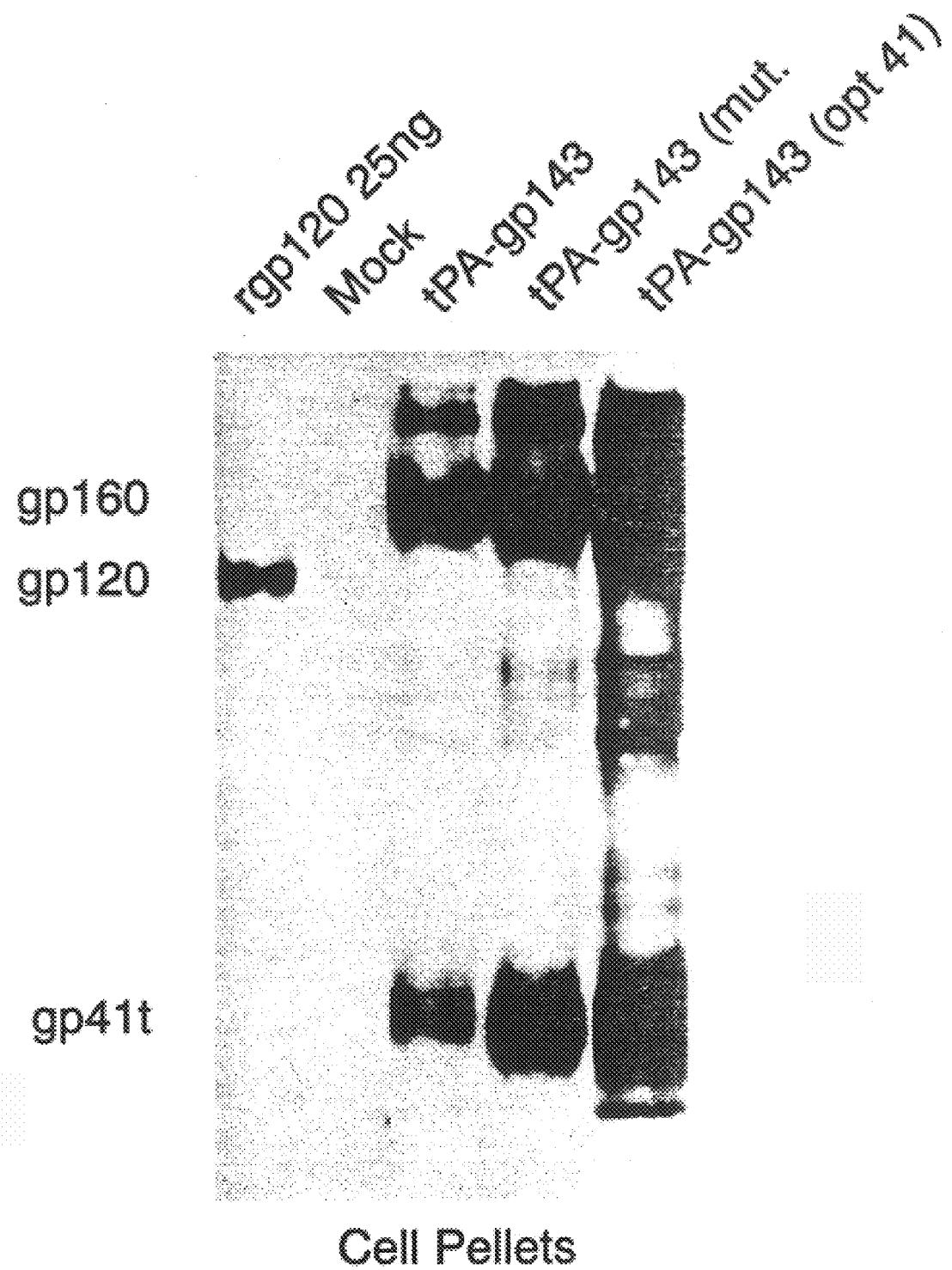

This construct was prepared by PCR using plasmid pF412 with the following sense and antisense PCR oligomers: 5'-GGT ACA TGA TCA CA GAA AAA TTG TGG GTC ACA GTC-3' (SEQ.ID21):, and 5'-CCA CAT TGA TCA G CCC GGG C TTA GGG TGA ATA GCC CTG CCT CAC TCT GTT CAC-3' (SEQ.ID:22). The resulting DNA segment contains BclI restriction sites at either end for cloning into V1Jns-tPA/BglII-digested with an SrfI site located immediately 3'- to the env open reading frame. Constructs were verified by DNA sequencing of ligation junctions and immunoblot analysis of transfected cells (FIG. 8).

B. V1Jns-tPA-gp143/mutRRE-A

This construct was based on IVA by excising the DNA segment using the unique MunI restriction enzyme site and the downstream SrfI site described above. This segment corresponds to a portion of the gp120 C5 domain and the entirety of gp32. A synthetic DNA segment corresponding to ~350 bp of the rev response element (RRE A) of gp160, comprised of optimal codons for translation, was joined to the remaining gp32 segment by splice overlap extension (SOE) PCR creating an AvrII restriction enzyme site at the junction of the two segments (but no changes in amino acid sequence). These PCR reactions were performed using the following sense and antisense PCR oligomers for generating the gp32-containing domain: 5'-CT GAA AGA CCA GCA ACT CCT AGG GAT TTG GGG TTG CTG TGG-3' (SEQ ID:23) and 5'-CCA CAT TGA TCA G CCC GGG C TTA GGG TGA ATA GCC CTG CCT CAC TCT GTT CAC-3' [SEQ ID:24] (which was used as the antisense oligomer for IVA), respectively. The mutated RRE (mutRRE-A) segment was joined to the wild type sequence of gp32 by SOE PCR using the following sense oligomer, 5'-GGT ACA CAA TTG GAG GAG CGA GTT ATA TAA ATA TAA G-3' (SEQ ID:25), and the antisense oligomer used to make the gp32 segment. The resulting joined DNA segment was digested with MunI and SrfI restriction enzymes and ligated into the parent gp143/MunI/SrfI digested plasmid. The resulting construct was verified by DNA sequencing of ligation and SOE PCR junctions and immunoblot analysis of transfected cells (FIG. 8).

C. V1Jns-tPA-gp143/mutRRE-B

This construct is similar to IVB except that the env proteolytic cleavage sites have been retained by using the mutRRE-B synthetic gene segment in place of mutRRE-A.

D. V1Jns-tPA-gp143/opt32-A

This construct was derived from IVB by AvrII and SrfI restriction enzyme digestion followed by ligation of a synthetic DNA segment corresponding to gp32 but comprised of optimal codons for translation (see gp32 opt below). The resulting products were verified by DNA sequencing of ligation junctions and immunoblot analysis.

E. V1Jns-tPA-gp143/opt32-B

This construct is similar to IVD except that the env proteolytic cleavage sites have been retained by using IVC as the initial plasmid.

F. V1Jns-tPA-gp143/SRV-1 3'-UTR

This construct is similar to IVA except that the 3'-UTR derived from the Simian Retrovirus-1 (SRV-1, see below) was inserted into the SrfI restriction enzyme site introduced immediately 3'- of the gp143 open reading frame. This UTR sequence has been described previously as facilitating rev-independent expression of HIV env and gag.

G. V1Jns-tPA-gp143/opt C1/opt32A

This construct was based on IVD, having a complete optimized codon segment for C5 and gp32 with an additional optimized codon segment (see below) replacing C1 at the amino terminus of gp120 following the tPA leader. The new C1 segment was joined to the remaining gp143 segment via SOE PCR using the following oligomers for PCR to synthesize the joined C1/143 segment: 5'-CCT GTG TGT GAG TTT AAA C TGC ACT GAT TTG AAG AAT GAT ACT AAT AC-3' (SEQ ID:26). The resulting gp143 gene contains optimal codon useage except for V1–V5 regions and has a unique PmeI restriction enzyme site placed at the junction of C1 and V1 for insertion of variable regions from other HIV genes.

H. V1Jns-tPA-gp143/opt C1/opt32B

This construct is similar to IVH except that the env proteolytic cleavage sites have been retained.

I. V1Jns-tPA-gp143/opt all-A

The env gene of this construct is comprised completely of optimal codons. The constant regions (C1, C5, gp32) are those described in 4B,D,H with an additional synthetic DNA segment corresponding to variable regions V1–V5 is inserted using a synthetic DNA segment comprised of optimal codons for translation.

J. V1Jns-tPA-gp143/opt all-B

This construct is similar to IVJ except that the env proteolytic cleavage sites have been retained.

K. V1Jns-tPA-gp143/opt all-A (Non-IIIB Strains)

This construct is similar to IIIG above except that env amino acid sequences from strains other than IIIB were used to determine optimum codon useage throughout the variable (V1–V5) regions.

L. V1Jns-tPA-gp143/opt all-B (Non-IIIB Strains)

This construct is similar to IIIG above except that env amino acid sequences from strains other than IIIB were used to determine optimum codon useage throughout the variable (V1–V5) regions.

EXAMPLE 10 gp143/glyB Vaccine Constructs

These constructs were prepared by PCR similarly as other tPA-containing constructs described above (tPA-gp120, tPA-gp140, tPA-gp143 and tPA-gp160), with the tPA leader in place of the native leader, but designed to produce COOH-terminated, membrane-bound env as with gp143. However, gp143/glyB constructs differ from gp143 in that of the six amino acids projected to comprise the intracellular peptide domain, the last 4 are the same those at the carboxyl terminus of human glycophorin B (glyB) protein (projected intracellular amino acid sequence=NH$_2$-NRLIKA-COOH (SEQ.ID:27) with the underlined residues corresponding to glyB and "R" common to both env and glyB). This construct was designed with the purpose gaining additional env expression and directed targeting to the cell surface by completely eliminating any transcript or peptide region corresponding to the intracellular portion of env that might negatively impact expression or protein stability/transport to the cell surface by replacing this region with a peptide sequence from an abundantly expressed protein (glyB) having a short cytoplasmic domain (intracellular amino acid sequence=NH$_2$-RRLIKA-COOH). Constructs were prepared in two forms (A or B) depending upon whether the gp160 proteolytic cleavage sites were removed or retained as described above.

A. V1Jns-tPA-gp143/opt32-A/glyB

This construct is the same as IVD except that the following antisense PCR oligomer was used to replace the intracellular peptide domain of gp143 with that of glycophorin B as described above: 5'-CCA CAT GAT ATC G CCC GGG C TTA TTA GGC CTT GAT CAG CCG GTT CAC AAT GGA CAG CAC AGC-3' (SEQ ID:28).

B. V1Jns-tPA-gp143/opt32-B/glyB

This construct is similar to VA except that the env proteolytic cleavage sites have been retained.

C. V1Jns-tPA-gp143/opt C1/opt32-A/glyB

This construct is the same as VA except that the first constant region (C1) of gp120 is replaced by optimal codons for translation as with IVH.

D. V1Jns-tPA-gp143/opt C1/opt32-B/glyB

This construct is similar to VC except that the env proteolytic cleavage sites have been retained.

E. V1Jns-tPA-gp143/opt all-A/glyB

The env gene of this construct is comprised completely of optimal codons as described above.

F. V1Jns-tPA-gp143/opt all-B/glyB

This construct is similar to VE except that the env proteolytic cleavage sites have been retained.

G. V1Jns-tPA-gp143/opt all-A/glyB (Non-IIIB Strains)

This construct is similar to IIIG above except that env amino acid sequences from strains other than IIIB were used to determine optimum codon useage throughout the variable (V1–V5) regions.

H. V1Jns-tPA-gp143/opt all-B/glyB (Non-IIIB Strains)

This construct is similar to VG except that the env proteolytic cleavage sites have been retained.

HIV env Vaccine Constructs with Variable Loop Deletions

These constructs may include all env forms listed above (gp120, gp140, gp143, gp160, gp143/glyB) but have had variable loops within the gp120 region deleted during preparation (e.g., V1, V2, and/or V3). The purpose of these modifications is to eliminate peptide segments which may occlude exposure of conserved neutralization epitopes such as the CD4 binding site. For example, the following oligomer was used in a PCR reaction to create a V1/V2 deletion resulting in adjoining THE C1 and C2 segments: 5'-CTG ACC CCC CTG TGT GTG GGG GCT GGC AGT TGT AAC ACC TCA GTC ATT ACA CAG-3' (SEQ ID:29).

EXAMPLE 11A

Design of Synthetic Gene Segments for Increased env Gene Expression

Gene segments were converted to sequences having identical translated sequences (except where noted) but with alternative codon usage as defined by R. Lathe in a research article from *J. Molec. Biol.* Vol. 183, pp. 1–12 (1985) entitled "Synthetic Oligonucleotide Probes Deduced from Amino Acid Sequence Data: Theoretical and Practical Considerations". The methodology described below to increase rev-independent expression of HIV env gene segments was based on our hypothesis that the known inability to express this gene efficiently in mammalian cells is a consequence of the overall transcript composition. Thus, using alternative codons encoding the same protein sequence may remove the constraints on env expression in the absence of rev. Inspection of the codon usage within env revealed that a high percentage of codons were among those infrequently used by highly expressed human genes. The specific codon replacement method employed may be described as follows employing data from Lathe et al.:

1. Identify placement of codons for proper open reading frame.
2. Compare wild type codon for observed frequency of use by human genes (refer to Table 3 in Lathe et al.).
3. If codon is not the most commonly employed, replace it with an optimal codon for high expression based on data in Table 5.
4. Inspect the third nucleotide of the new codon and the first nucleotide of the adjacent codon immediately 3'- of the first. If a 5'-CG-3' pairing has been created by the new codon selection, replace it with the choice indicated in Table 5.
5. Repeat this procedure until the entire gene segment has been replaced.
6. Inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences.
7. Assemble synthetic gene segments and test for improved expression.

These methods were used to create the following synthetic gene segments for HIV env creating a gene comprised entirely of optimal codon usage for expression: (i) gp120-C1 (opt); (ii) V1–V5 (opt); (iii) RRE-A/B (mut or opt); and (iv) gp30 (opt) with percentages of codon replacements/nucleotide substitutions of 56/19, 73/26, 78/28, and 61/25 obtained for each segment, respectively. Each of these segments has been described in detail above with actual sequences listed below.

gp120-C1 (opt)

This is a gp120 constant region 1 (C1) gene segment from the mature N-terminus to the beginning of V1 designed to have optimal codon usage for expression.

1 TGATCACAGA GAAGCTGTGG GTGACAGTGT ATTATGGCGT GCCAGTCTGG 51 AAGGAGGCCA CCACCACCCT GTTCTGTGCC TCTGATGCCA AGGCCTATGA 101 CACAGAGGTG CACAATGTGT GGGCCACCCA TGCCTGTGTG CCCACAGACC 151 CCAACCCCCA GGAGGTGGTG CTGGTGAATG TGACTGAGAA CTTCAACATG 201 TGGAAGAACA ACATGGTGGA GCAGATGCAT GAGGACATCA TCAGCCTGTG 251 GGACCAGAGC CTGAAGCCCT GTGTGAAGCT GACCCCCCTG TGTGTGAGTT 301 TAAAC (SEQ ID:30)

MN V1–V5 (opt)

This is a gene segment corresponding to the derived protein sequence for HIV MN V1–V5 (1066BP) having optimal codon usage for expression.

1 AGTTTAAACT GCACAGACCT GAGGAACACC ACCAACACCA ACAACTCCAC 51 AGCCAACAAC AACTCCAACT CCGAGGGCAC CATCAAGGGG GGGGAGATGA 101 AGAACTGCTC CTTCAACATC ACCACCTCCA TCAGGGACAA GATGCAGAAG 151 GAGTATGCCC TGCTGTACAA GCTGGACATT GTGTCCATTG ACAATGACTC 201 CACCTCCTAC AGGCTGATCT CCTGCAACAC CTCTGTCATC ACCCAGGCCT 251 GCCCCAAAAT CTCCTTTGAG CCCATCCCCA TCCACTACTG TGCCCCTGCT 301 GGCTTTGCCA TCCTGAAGTG CAATGACAAG AAGTTCTCTG GCAAGGGCTC 351 CTGCAAGAAT GTGTCCACAG TGCAGTGCAC ACATGGCATC AGGCCTGTGG 401 TGTCCACCCA GCTGTCGTCG AATGGCTCCC TGGCTGAGGA GGAGGTGGTC 451 ATCAGGTCTG AGAACTTCAC AGACAATGCC AAGACCATCA TCGTCGACCT 501 GAATGAGTCT GTGCAGATCA ACTGCACCAG GCCCAACTAC AACAAGAGGA 551 AGAGGATCCA CATTGGCCCT GGCAGGGCCT TCTACACCAC CAAGAACATC 601 ATTGGCACCA TCAGGCAGGC CCACTGCAAC ATCTCCAGGG CCAAGTGGAA 651 TGACACCCTG AGGCAGCTTG TGTCCAAGCT GAAGGAGCAG TTCAAGAACA 701 AGACCATTGT GTTCAACCAG TCCTCTGGGG GGGACCCTGA GATTGTGATG 751 CACTCCTTCA ACTGTGGGGG GGAGTTCTTC TACTGCAACA CCTCCCCCCT 801 GTTCAACTCC ACCTGGAATG GCAACAACAC CTGGAACAAC ACCACAGGCT 851 CCAACAACAA CATCACCCTC CAGTGCAAGA TCAAGCAGAT CATCAACATG 901 TGGCAGGAGG TGGGCAAGGC CATGTATGCC CCCCCCATTG AGGGCCAGAT 951 CAGGTGCTCC TCCAACATCA CAGGCCTGCT GCTGACCAGG GATGGGGGGA 1001 AGGACACAGA CACCAACGAC ACCGAATCT TCAGGCCTGG GGGGGGGGAC 1051 ATGAGGGACA ATTGG (SEQ ID:31)

RRE.MUT (A)

This is a DNA segment corresponding to the rev response element (RRE) of HIV-1 comprised of optimal codon usage for expression. The "A" form also has removed the known proteolytic cleavage sites at the gp120/gp41 junction by using the nucleotides indicated in boldface.

1 GACAATTGGA GGAGCGAGTT ATATAAATAT AAGGTGGTGA AGATTGAGCC 51 CCTGGGGGTG GCCCCAACAA AAGCT CAGAACCACGTGGTGCAGAACGAGC101 ACCAGGCCGT GGGCATTGGG GCCCTGTTTC TGGGCTTTCT GGGGGCTGCT 151 GGCTCCACAA TGGGCGCCGC TAGCATGACC CTCACCGTGC AAGCTCGCCA 201 GCTGCTGAGT GGCATCGTCC AGCAGCAGAA CAACCTGCTC CGCGCCATCG 251 AAGCCCAGCA GCACCTCCTC CAGCTGACTG TGTGGGGGAT CAAACAGCTT 301 CAGGCCCGGG TGCTGGCCGT CGAGCGCTAT CTGAAAGACC AGCAACTCCT 351 AGGC (SEQ ID:32)

RRE.Mut (B)

This is a DNA segment corresponding to the rev response element (RRE) of HIV-1 comprised of optimal codon usage for expression. The "B" form retains the known proteolytic cleavage sites at the gp120/gp41 junction.

1 GACAATTGGA GGAGCGAGTT ATATAAATAT AAGGTGGTGA AGATTGAGCC 51 CCTGGGGGTG GCCCCAACAA AAGCT AAGAGAAGAGTGGTGCAGAGAGAGA101 AGAGAGCCGT GGGCATTGGG GCCCTGTTTC TGGGCTTTCT GGGGGCTGCT 151 GGCTCCACAA TGGGCGCCGC TAGCATGACC CTCACCGTGC AAGCTCGCCA 201 GCTGCTGAGT GGCATCGTCC AGCAGCAGAA CAACCTGCTC CGCGCCATCG 251 AAGCCCAGCA GCACCTCCTC CAGCTGACTG TGTGGGGGAT CAAACAGCTT 301 CAGGCCCGGG TGCTGGCCGT CGAGCGCTAT CTGAAAGACC AGCAACTCCT 351 AGGC (SEQ ID:33)

gp32 (opt)

This is a gp32 gene segment from the AvrII site (starting immediately at the end of the RRE) to the end of gp143 comprised of optimal codons for expression.

```
1 CCTAGGCA TCTGGGGCTG CTCTGGCAAG
  CTGATCTGCA CCACAGCTGT 51 GCCCTGGAAT
  GCCTCCTGGT CCAACAAGAG CCTGGAGCAA
  ATCTGGAACA 101 ACATGACCTG GATG-
  GAGTGG GACAGAGAGA TCAACAACTA CAC-
  CTCCCTG 151 ATCCACTCCC TGATTGAGGA
  GTCCCAGAAC CAGCAGGAGA AGAATGAGCA
  201 GGAGCTGCTG GAGCTGGACA AGTGGGC-
  CTC CCTGTGGAAC TGGTTCAACA 251 TCAC-
  CAACTG GCTGTGGTAC ATCAAAATCT TCAT-
  CATGAT TGTGGGGGGC 301 CTGGTGGGGC
  TGCGGATTGT CTTTGCTGTG CTGTCCATTG
  TGAACCGGGT 351 GAGACAGGGC TACTC-
  CCCCT ATTAAGCCCG GGCGATATC (SEQ ID:34)
```

SRV-1 CTE (A)

This is a synthetic gene seg membrane-bound influenza HA constructs for immunogenicity [Ulmer et al., Science 259:1745–1749, 1993; Montgomery, D., et al., *DNA and Cell Biol.*, 12:777–783, 1993]. gp160 retains substantial rev dependence even with a heterologous leader peptide sequence so that further constructs were made to increase expression in the absence of rev.

EXAMPLE 13
Assay for HIV Cytotoxic T-Lymphocytes

The methods described in this section illustrate the assay as used for vaccinated mice. An essentially similar assay can be used with primates except that autologous B cell lines must be established for use as target cells for each animal. This can be accomplished for humans using the Epstein-Barr virus and for rhesus monkey using the herpes B virus.

Peripheral blood mononuclear cells (PBMC) are derived from either freshly drawn blood or spleen using Ficoll-Hypaque centrifugation to separate erythrocytes from white blood cells. For mice, lymph nodes may be used as well. Effecter CTLs may be prepared from the PBMC either by in vitro culture in IL-2 (20 U/ml) and concanavalin A (2 $\mu$g/ml) for 6–12 days or by using specific antigen using an equal number of irradiated antigen presenting cells. Specific antigen can consist of either synthetic peptides (9–15 amino acids usually) that are known epitopes for CTL recognition for the MHC haplotype of the animals used, or vaccinia virus constructs engineered to express appropriate antigen. Target cells may be either syngeneic or MHC haplotype-matched cell lines which have been treated to present appropriate antigen as described for in vitro stimulation of the CTLs. For Balb/c mice the P18 peptide (ArgIleHisIleGlyProGlyArgAlaPheTyrThrThrLysAsn [SEQ.ID:37], for HIV MN strain) can be used at 10 $\mu$M concentration to restimulate CTL in vitro using irradiated syngeneic splenocytes and can be used to sensitize target cells during the cytotoxicity assay at 1–10 $\mu$M by incubation at 37° C. for about two hours prior to the assay. For these H-$2^d$ MHC haplotype mice, the murine mastocytoma cell line, P815, provides good target cells. Antigen-sensitized target cells are loaded with Na$^{51}$CrO$_4$, which is released from the interior of the target cells upon killing by CTL, by incubation of targets for 1–2 hours at 37° C. (0.2 mCi for ~5×10$^6$ cells) followed by several washings of the target cells. CTL populations are mixed with target cells at varying ratios of effectors to targets such as 100:1, 50:1, 25:1, etc., pelleted together, and incubated 4–6 hours at 37° C. before harvest of the supernatants which are then assayed for release of radioactivity using a gamma counter. Cytotoxicity is calculated as a percentage of total releasable counts from the target cells (obtained using 0.2% Triton X-100 treatment) from which spontaneous release from target cells bas been subtracted.

EXAMPLE 14
Assay For HIV Specific Antibodies

ELISA were designed to detect antibodies generated against HIV using either specific recombinant protein or synthetic peptides as substrate antigens. 96 well microtiter plates were coated at 4° C. overnight with recombinant antigen at 2 $\mu$g/ml in PBS (phosphate buffered saline) solution using 50 $\mu$l/well on a rocking platform. Antigens consisted of either recombinant protein (gp120, rev: Repligen Corp.; gp160, gp41: American Bio-Technologies, Inc.) or synthetic peptide (V3 peptide corresponding to virus isolate sequences from IIIB, etc.: American Bio-Technologies, Inc; gp41 epitope for monoclonal antibody 2F5). Plates were rinsed four times using wash buffer (PBS/0.05% Tween 20) followed by addition of 200 $\mu$l/well of blocking buffer (1% Carnation milk solution in PBS/0.05% Tween-20) for 1 hr at room temperature with rocking. Pre-sera and immune sera were diluted in blocking buffer at the desired range of dilutions and 100 $\mu$l added per well. Plates were incubated for 1 hr at room temperature with rocking and then washed four times with wash buffer. Secondary antibodies conjugated with horse radish peroxidase, (anti-rhesus Ig, Southern Biotechnology Associates; anti-mouse and anti-rabbit Igs, Jackson Immuno Research) diluted 1:2000 in blocking buffer, were then added to each sample at 100 $\mu$l/well and incubated 1 hr at room temperature with rocking. Plates were washed 4 times with wash buffer and then developed by addition of 100 $\mu$l/well of an o-phenylenediamine (o-PD, Calbiochem) solution at 1 mg/ml in 100 mM. citrate buffer at pH 4.5. Plates were read for absorbance at 450 nm both kinetically (first ten minutes of reaction) and at 10 and 30 minute endpoints (Thermo-max microplate reader, Molecular Devices).

EXAMPLE 15
Assay for HIV Neutralizing Antibodies

In vitro neutralization of HIV isolates assays using sera derived from vaccinated animals was performed as follows. Test sera and pre-immune sera were heat inactivated at 56° C. for 60 min before use. A titrated amount of HIV-1 was added in 1:2 serial dilutions of test sera and incubated 60 min at room temperature before addition to 10$^5$ MT-4 human lymphoid cells in 96 well microtiter plates. The virus/cell mixtures were incubated for 7 days at 37° C. and assayed for virus-mediated killing of cells by staining cultures with tetrazolium dye. Neutralization of virus is observed by prevention of virus-mediated cell death.

EXAMPLE 16
Isolation of Genes from Clinical HIV Isolates

HIV viral genes were cloned from infected PBMC's which had been activated by ConA treatment. The preferred method for obtaining the viral genes was by PCR amplification from infected cellular genome using specific oligomers flanking the desired genes. A second method for obtaining viral genes was by purification of viral RNA from the supernatants of infected cells and preparing cDNA from this material with subsequent PCR. This method was very analogous to that described above for cloning of the murine B7 gene except for the PCR oligomers used and random hexamers used to make cDNA rather than specific priming oligomers.

Genomic DNA was purified from infected cell pellets by lysis in STE solution (10 mM NaCl, 10 mM EDTA, 10 mM Tris-HCl, pH 8.0) to which Proteinase K and SDS were added to 0.1 mg/ml and 0.5% final concentrations, respectively. This mixture was incubated overnight at 56° C. and extracted with 0.5 volumes of phenol:chloroform:isoamyl alcohol (25:24:1). The aqueous phase was then precipitated by addition of sodium acetate to 0.3 M final concentration and two volumes of cold ethanol. After pelleting the DNA from solution the DNA was resuspended in 0.1× TE solution (1× TE=10 mM Tris-HCl, pH 8.0, 1 mM EDTA). At this point SDS was added to 0.1% with 2 U of RNAse A with incubation for 30 minutes at 37° C. This solution was extracted with phenol/chloroform/isoamyl alcohol and then precipitated with ethanol as before. DNA was suspended in 0.1× TE and quantitated by measuring its ultraviolet absorbance at 260 nm. Samples were stored at –20° C. until used for PCR.

PCR was performed using the Perkin-Elmer Cetus kit and procedure using the following sense and antisense oligomers for gp160: 5'-GA AAG AGC AGA AGA CAG TGG CAA TGA-3' (SEQ.ID:38) and 5'-GGG CTT TGC TAA ATG GGT GGC AAG TGG CCC GGG C ATG TGG-3' (SEQ.ID:39), respectively. These oligomers add an SrfI site at the 3'-terminus of the resulting DNA fragment. PCR-derived segments are cloned into either the V1Jns or V1R vaccination vectors and V3 regions as well as ligation junction sites confimed by DNA sequencing.

EXAMPLE 17

T Cell Proliferation Assays

PBMCs are obtained and tested for recall responses to specific antigen as determined by proliferation within the PBMC population. Proliferation is monitored using $^3$H-thymidine which is added to the cell cultures for the last 18–24 hours of incubation before harvest. Cell harvesters retain isotope-containing DNA on filters if proliferation has occurred while quiescent cells do not incorporate the isotope which is not retained on the filter in free form. For either rodent or primate species $4\times10^5$ cells are plated in 96 well microtiter plates in a total of 200 µl of complete media (RPMI/10% fetal calf serum). Background proliferation responses are deternined using PBMCs and media alone while nonspecific responses are generated by using lectins such as phytohaemagglutin (PHA) or concanavalin A (ConA) at 1–5 µg/ml concentrations to serve as a positive control. Specific antigen consists of either known peptide epitopes, purified protein, or inactivated virus. Antigen concentrations range from 1–10 µM for peptides and 1–10 µg/ml for protein. Lectin-induced proliferation peaks at 3–5 days of cell culture incubation while antigen-specific responses peak at 5–7 days. Specific proliferation occurs when radiation counts are obtained which are at least three-fold over the media background and is often given as a ratio to background, or Stimulation Index (SI). HIV gp160 is known to contain several peptides known to cause T cell proliferation of gp160/gp120 immunized or HIV-infected individuals. The most commonly used of these are: T1 (LysGlnIleIleAsnMetTrpGlnGluValGlyLysAlaMetTyrAla [SEQ.ID:40]); T2 (HisGluAspIleIleSerLeuTrpAspGlnSerLeuLys [SEQ.ID:41]; and, TH4 (AspArgValIleGluValValGlnGlyAlaTyrArgAlaIleArg [SEQ.ID:42]). These peptides have been demonstrated to stimulate proliferation of PBMC from antigen-sensitized mice, nonhuman primates, and humans.

EXAMPLE 18

Vector V1R Preparation

In an effort to continue to optimize our basic vaccination vector, we prepared a derivative of V1Jns which was designated as V1R. The purpose for this vector construction was to obtain a minimum-sized vaccine vector, i.e., without unnecessary DNA sequences, which still retained the overall optimized heterologous gene expression characteristics and high plasmid yields that V1J and V1Jns afford. We determined from the literature as well as by experiment that (1) regions within the pUC backbone comprising the E. coli origin of replication could be removed without affecting plasmid yield from bacteria; (2) the 3'-region of the kan$^r$ gene following the kanamycin open reading frame could be removed if a bacterial terminator was inserted in its stead; and, (3) ~300 bp from the 3'-half of the BGH terminator could be removed without affecting its regulatory function (following the original KpnI restriction enzyme site within the BGH element).

V1R was constructed by using PCR to synthesize three segments of DNA from V1Jns representing the CMVintA promoter/BGH terminator, origin of replication, and kanamycin resistance elements, respectively. Restriction enzymes unique for each segment were added to each segment end using the PCR oligomers: SspI and XhoI for CMVintA/BGH; EcoRV and BamHI for the kan$^r$ gene; and, BclI and SalI, for the ori$^r$. These enzyme sites were chosen because they allow directional ligation of each of the PCR-derived DNA segments with subsequent loss of each site: EcoRV and SspI leave blunt-ended DNAs which are compatible for ligation while BamHI and BclI leave complementary overhangs as do SalI and XhoI. After obtaining these segments by PCR each segment was digested with the appropriate restriction enzymes indicated above and then ligated together in a single reaction mixture containing all three DNA segments. The 5'-end of the ori$^r$ was designed to include the T2 rho independent terminator sequence that is normally found in this region so that it could provide termination information for the kanamycin resistance gene. The ligated product was confirmed by restriction enzyme digestion (>8 enzymes) as well as by DNA sequencing of the ligation junctions. DNA plasmid yields and heterologous expression using viral genes within V1R appear similar to V1Jns. The net reduction in vector size achieved was 1346 bp (V1Jns=4.86 kb; V1R=3.52 kb), [SEQ.ID:43 of this specification; also see FIG. 11 and SEQ ID:100 of WO95/24485; PCT International Application No. PCT/US95/02633].

PCR oligomer sequences used to synthesize V1R (restriction enzyme sites are underlined and identified in brackets following sequence):

(1) 5'-GGT ACA AAT ATT GG CTA TTG GCC ATT GCA TAC G-3' [SspI], (SEQ.ID:44):, (2) 5'-CCA CAT CTC GAG GAA CCG GGT CAA TTC TTC AGC ACC-3' [XhoI], (SEQ.ID:45): (for CMVintA/BGH segment)

(3) 5'-GGT ACA GAT ATC GGA AAG CCA CGT TGT GTC TCA AAA TC-3'[EcoRV], (SEQ.ID:46):

(4) 5'-CCA CAT GGA TCC G TAA TGC TCT GCC AGT GTT ACA ACC-3' [BamHI], (SEQ.ID:47): (for kanamycin resistance gene segment)

(5) 5'-GGT ACA TGA TCA CGT AGA AAA GAT CAA AGG ATC TTC TTG-3'[BclI], (SEQ.ID:48):, (6) 5'-CCA CAT GTC GAC CC GTA AAA AGG CCG CGT TGC TGG-3' [SalI], (SEQ.ID:49): (for E. coli origin of replication)

Ligation junctions were sequenced for V1R using the following oligomers:

5'-GAG CCA ATA TAA ATG TAC-3' (SEQ.ID:50): [CMVintA/kan$^r$ junction]

5'-CAA TAG CAG GCA TGC-3' (SEQ.D:51): [BGH/ori junction]

5'-G CAA GCA GCA GAT TAC-3' (SEQ.ID:52): [ori/kan$^r$ junction]

EXAMPLE 19

Heterologous Expression of HIV Late Gene Products

HIV structural genes such as env and gag require expression of the HIV regulatory gene, rev, in order to efficiently produce full-length proteins. We have found that rev-dependent expression of gag yielded low levels of protein and that rev itself may be toxic to cells. Although we achieved relatively high levels of rev-dependent expression of gp160 in vitro this vaccine elicited low levels of antibodies to gp160 following in vivo immunization with rev/gp160 DNA. This may result from known cytotoxic effects of rev as well as increased difficulty in obtaining rev function in myotubules containing hundreds of nuclei (rev protein needs to be in the same nucleus as a rev-dependent transcript in order for gag or env protein expression to occur). However, it has been possible to obtain rev-independent expression using selected modifications of the env gene.

1. rev-independent Expression of env

In general, our vaccines have utilized primarily HIV (IIIB) env and gag genes for optimization of expression within our generalized vaccination vector, V1Jns, which is comprised of a CMV immediate-early (IE) promoter, a BGH-derived polyadenylation and transcriptional termination sequence, and a pUC backbone. Varying efficiencies, depending upon how large a gene segment is used (e g., gp120 vs. gp160), of rev-independent expression may be achieved for env by replacing its native secretory leader peptide with that from the tissue-specific plasminogen activator (tPA) gene and expressing the resulting chimeric gene behind the CMVIE promoter with the CMV intron A. tPA-gp120 is an example of a secreted gp120 vector constructed in this fashion which functions well enough to elicit anti-gp120 immune responses in vaccinated mice and monkeys.

Because of reports that membrane-anchored proteins may induce much more substantial (and perhaps more specific for HIV neutralization) antibody responses compared to secreted proteins as well as to gain additional epitopes, we prepared V1Jns-tPA-gp160 and V1Jns-rev/gp160. The tPA-gp160 vector produced detectable quantities of gp160 and gp120, without the addition of rev, as shown by immunoblot analysis of transfected cells, although levels of expression were much lower than that obtained for rev/gp160, a rev-dependent gp160-expressing plasmid. This is probably because inhibitory regions, which confer rev dependence upon the gp160 transcript, occur at multiple sites within gp160 including at the COOH-terminus of gp41. A vector was prepared for a COOH-terminally truncated form of tPA-gp160 (tPA-gp143) which was designed to increase the overall expression levels of env by elimination of these inhibitory sequences. The gp143 vector also eliminates intracellular gp41 regions containing peptide motifs (such as Leu-Leu) known to cause diversion of membrane proteins to the lysosomes rather than the cell surface. Thus, gp143 may be expected to have increased levels of expression of the env protein (by decreasing rev-dependence) and greater efficiency of transport of protein to the cell surface compared to full-length gp160 where these proteins may be better able to elicit anti-gp160 antibodies following DNA vaccination. tPA-gp143 was further modified by extensive silent mutagenesis of the rev response element (RRE) sequence (350 bp) to eliminate additional inhibitory sequences for expression. This construct, gp143/mutRRE, was prepared in two forms: either eliminating (form A) or retaining (form B) proteolytic cleavage sites for gp120/41. Both forms were prepared because of literature reports that vaccination of mice using uncleavable gp160 expressed in vaccinia elicited much higher levels of antibodies to gp160 than did cleavable forms.

A quantitative ELISA for gp160/gp120 expression in cell transfectants was developed to determine the relative expression capabilities for these vectors. In vitro transfection of 293 cells followed by quantification of cell-associated vs. secreted/released gp120 yielded the following results: (1) tPA-gp160 expressed 5–10× less gp120 than rev/gp160 with similar proportions retained intracellularly vs. released from the cell surface; (2) tPA-gp143 gave 3–6× greater secretion of gp120 than rev/gp160 with only low levels of cell-associated gp143, confirming that the cytoplasmic tail of gp160 causes intracellular retention of gp160 which can be overcome by partial deletion of this sequence; and, (3) tPA-gp143/mutRRE A and B gave ~10× greater expression levels of protein than did parental tPA-gp143 while elimination of proteolytic processing was confirmed for form A.

Thus, our strategy to increase rev-independent expression has yielded stepwise increases in overall expression levels as well as redirecting membrane-anchored gp143 to the cell surface away from lysosomes. It is important to note that this is a generic construct into which it should be possible to insert gp120 sequences derived from various primary viral isolates within a vector cassette containing these modifications which reside either at the $NH_2$-terminus (tPA leader) or COOH-terminus (gp41), where few antigenic differences exist between different viral strains.

FIGS. 2–7 present data supporting the use of various constructs, including but not limited to a gp143-based construct, and preferably a tPA-gp143 based construct, as a DNA vaccine against HIV infection. FIG. 2 shows that tPA-143 (opt41) elicits an anti-gp120 antibody response in the in the range of GMT=$10^3$. FIG. 3 measures and compares anti-gp120 antibody titers for several DNA vaccines, including gp143-based constructs. FIG. 4 shows the relative expression of tPA-gp143 and tPA-143/mutRRE in comparison to the tPA-gp160 construct. FIG. 5 measures generation of anti-gp120 antibodies for both the optA and optB forms of tPA-gp143 constructs. FIG. 6 shows the ability of several DNA vaccines, including tPA-gp143-optA and tPA-gp143-optB, to promote generation of neutralizing antibodies against HIV strains subsequent to murine DNA vaccination. FIG. 7 also shows HIV neutralization data for various DNA vaccine constructions, including tPA-gp143-optA, tPA-gp143-optB, tPA-gp143-optA-glyB and tPA-gp143-optB-glyB.

2. Expression of gp120 Derived from a Clinical Isolate

To apply these expression strategies to viruses that are relevant for vaccine purposes and confirm the generality of our approaches, we also prepared a tPA-gp120 vector derived from a primary HIV isolate (containing the North American concensus V3 peptide loop; macrophage-tropic and nonsyncytia-inducing phenotypes). This vector gave high expression/secretion of gp120 with transfected 293 cells and elicited anti-gp120 antibodies in mice thus demonstrating that it was cloned in a functional form. Primary isolate gp160 genes will also be used for expression in the same way as for gp160 derived from laboratory strains.

3. Immune Responses to HIV-1 env Polynucleotide Vaccines

Effect of vaccination route on immune responses in mice: While efforts to improve expression of gp160 are ongoing, we have utilized the tPA-gp 120 DNA construct to assess immune responses and ways to augment them. Intramuscular (i.m.) and intradermal (i.d.) vaccination routes were compared for this vector at 100, 10, and 1 μg doses in mice. Vaccination by either route elicited antibody responses (GMTs=$10^3$–$10^4$) in all recipients following 2–3 vaccinations at all three dosage levels. Each route elicited similar anti-gp120 antibody titers with clear dose-dependent responses. However, we observed greater variability of responses for i.d. vaccination, particularly at the lower doses following the initial inoculation. Moreover, helper T-cell responses, as determined by antigen-specific in vitro proliferation and cytokine secretion, were higher following i.m. vaccination than i.d. We concluded that i.d. vaccination did not offer any advantages compared to i.m. for this vaccine.

4. gp120 DNA Vaccine-mediated Helper T Cell Immunity in Mice gp120 DNA vaccination produced potent helper T-cell responses in all lymphatic compartments tested (spleen, blood, inguinal, mesenteric, and iliac nodes) with $T_H1$-like cytokine secretion profiles (i.e., g-interferon and IL-2 production with little or no IL-4). These cytokines generally promote strong cellular immunity and have been associated with maintenance of a disease-free state for HIV-seropositive patients. Lymph nodes have been shown to be primary sites for HIV replication, harboring large reservoirs of virus even when virus cannot be readily detected in the blood. A vaccine which can elicit anti-HIV immune responses at a variety of lymph sites, such as we have shown with our DNA vaccine, may help prevent successful colonization of the lymphatics following initial infection.

5. env DNA Vaccine-mediated Antibody Responses

African green (AGM) and Rhesus (RHM) monkeys which received gp120 DNA vaccines showed low levels of neutralizing antibodies following 2–3 vaccinations, which could not be increased by additional vaccination. These results, as well as increasing awareness within the HIV vaccine field that oligomeric gp160 is probably a more relevant target antigen for eliciting neutralizing antibodies than gp120 monomers, have led us to focus upon obtaining effective expression of gp160-based vectors (see above). Mice and AGM were also vaccinated with the primary isolate derived tPA-gp120 vaccine. These animals exhibited anti-V3 peptide (using homologous sequence) reciprocal endpoint antibody titers ranging 500–5000, demonstrating that this vaccine design is functional for clinically relevant viral isolates.

The gp160-based vaccines, rev-gp160 and tPA-gp160, failed to consistently elicit antibody responses in mice and nonhuman primates or yielded low antibody titers. Our initial results with the tPA-gp143 plasmid yielded geometric mean titers (GMT)>$10^3$ in mice and AGM following two vaccinations. These data indicate that we have signficantly improved the immunogenicity of gp160-like vaccines by increasing expression levels and more efficient intracellular trafficking of env to the cell surface. This construct, as well as the tPA-gp143/mutRRE A and B vectors, will continue to be characterized for antibody responses, especially for virus neutralization.

6. env DNA Vaccine-mediated CTL Responses in Monkeys

We continued to characterize CTL responses of RHM that had been vaccinated with gp120 and gp160/IRES/rev DNA. All four monkeys that received this vaccine showed significant MHC Class I-restricted CTL activities (20–35% specific killing at an effector/target=20) following two vaccinations. Following a fourth vaccination these activities increased to 50–60% killing under similar test conditions, indicating that additional vaccination boosted responses significantly. The CTL activities have persisted for at least seven months subsequent to the final vaccination at about 50% of their peak levels indicating that long-term memory had been established.

EXAMPLE 20

SIV/HTV (SHIV) Chimeras

A major obstacle for testing the protective efficacy of candidate HIV-1 vaccines has been the lack of a suitable animal challenge model for this virus. Although the simian immunodeficiency virus (SIV), which is closely related to HIV, is infectious and causes AIDS in rhesus monkeys, the only animal species which can be infected with HIV-1 viral isolates is the chimpanzee. However, the resulting viremia from this infection is low-level, transient, and no pathogenic effects (e.g., lymphopenia, immunodeficiency-related opportunistic infections, etc.) develop. Recently, hybrid viruses comprised of SIV and HIV genomes have been developed which are also infectious to rhesus monkeys and which can cause infection-related AIDS. An example of this type of virus is SHIV-4 (IIIB) (Li et.al., J. of Acquired Immune Deficiency Syndrome, Vol. 5, 639–646 (1992)). This virus contains the SIV (MAC239) genome except for the regulatory genes, tat and rev, and the structural gene, env. Because the principle component of candidate HIV vaccines is based upon env this virus allows testing vaccines developed for human clinical purposes for protective efficacy against infection in an animal model.

EXAMPLE 21

Plasmid DNA and Recombinant Protein Combination Vaccines

Figure 9:
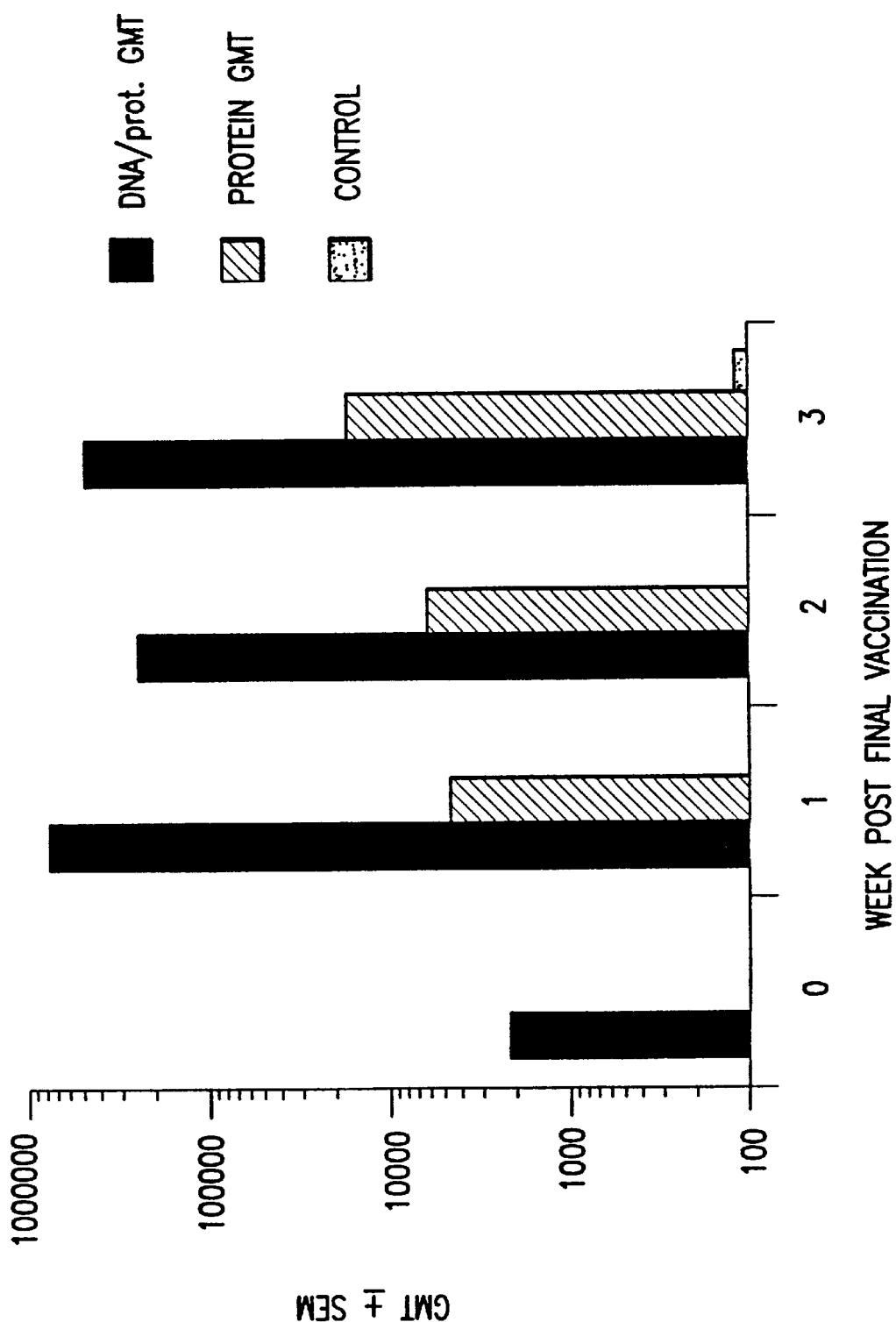
Figure 10:
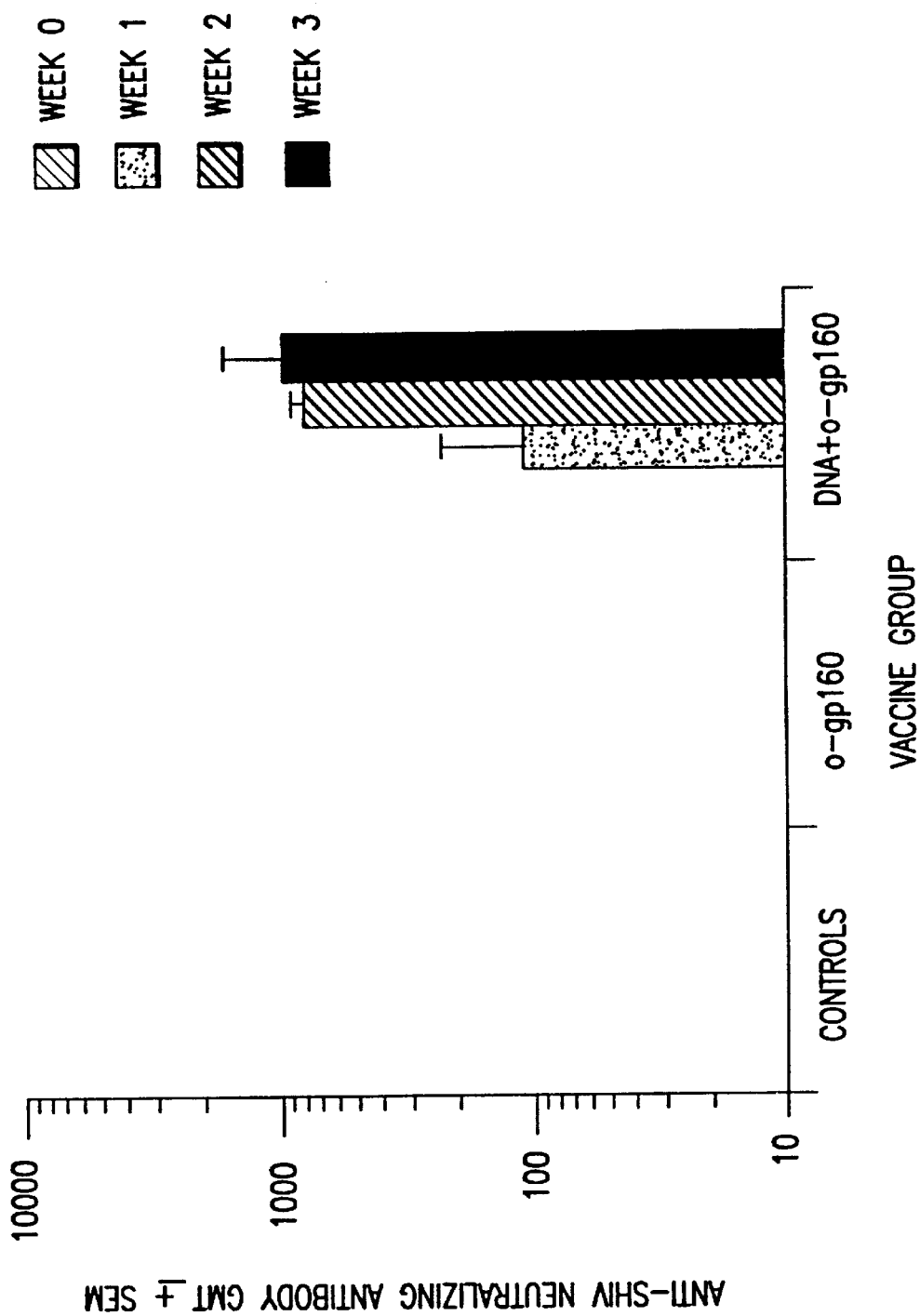

Vaccines having both a plasmid DNA HIV env component and a recombinant HIV env protein component were tested for their abilities to induce antibody responses in rhesus monkeys. FIG. 9 and FIG. 10 show the resulting anti-gp120 ELISA antibody and SHIV-4 (IIIB) virus neutralizing antibody titers, respectively, following vaccination of rhesus with HIV env gene-containing DNA vaccines and recombinant protein (formulated in an appropriate adjuvant). These monkeys developed high titers of env-specific antibodies and neutralizing antibodies. Control monkeys, vaccinated with "blank" DNA that did not contain a gene and ovalbumin did not develop any detectable env-specific responses while monkeys vaccinated only with the protein component of this vaccine showed low levels of antigen-specific antibodies detected by ELISA and no neutralizing antibodies. When these monkeys were challenged with SHIV-4 (IIIB) virus all control and protein only monkeys became infected while those receiving both env DNA and protein did not develop a detectable SHIV viremia. These monkeys are currently being tested periodically for possible delayed onset of infection.

What is claimed is:

1. A synthetic polynucleotide comprising a DNA sequence encoding HIV env protein or a fragment thereof, the DNA sequence comprising codons optimized for expression in a mammalian host, wherein said synthetic polynucleotide is selected from the group consisting of:

a) V1Jns-tPA-HIV$_{MN}$ gp120, wherein the 5' end which is SEQ ID NO:4 and the 3' end which is SEQ ID NO:5;

b) V1Jns-tPA-HIV$_{IIIB}$ gp120, wherein the 5' end which is SEQ ID NO:6 and the 3' end which is SEQ ID NO:7;

c) V1Jns-tPA-gp160/opt C1/opt41-A and V1Jns-tPA-gp160/opt C1/opt41-B, wherein the opt C1 comprises SEQ ID NO:30, and the gp120/41 proteolytic cleavage sites is retained in the "B" form (SEQ ID NO:33) and eliminated in the "A" form (SEQ ID NO:32);

d) V1Jns-tPA-gp160/opt all-A, V1Jns-tPA-gp160/opt all-B, V1Jns-tPA gp160/opt all-A (non$_{IIIB}$ strains); V1Jns-tPA-gp160/opt all-B (non$_{IIIB}$ strains), wherein the optimized codon usage is derived from opt C1 (SEQ ID NO:30), and wherein the gp160 proteolytic cleavage site is retained in form "B" (SEQ ID NO:33) and is eliminated in form "A" (SEQ ID NO:32);

e) V1Jns-tPA-gp143, V1Jns-tPA-gp143/mutRRE-A, and V1Jns-tPA-gp143/mutRRE-B, wherein the gp160 proteolytic cleavage site is retained in form "B" (SEQ ID NO:33) and is eliminated in form "A" (SEQ ID NO:32);

f) V1Jns-tPA-gp143/opt32-A and V1Jns-tPA-gp143/opt32-B, comprising a gp 32 opt sequence (SEQ ID NO:34), and wherein the gp160 proteolytic cleavage site is retained in form "B" (SEQ ID NO:33) and is eliminated in form "A" (SEQ ID NO:32);

g) V1Jns-tPA-gp143/SRV-1 3'-UTR, wherein the SRV-1 3' UTR comprises SEQ ID NO:35;

h) V1Jns-tPA-gp143/opt C1/opt32A and V1Jns-tPA-gp143/opt C1/opt32B, wherein the optimized codon usage is derived from opt C1 (SEQ ID NO:30), and gp 32 opt (SEQ ID NO:34), and wherein the gp160 proteolytic cleavage site is retained in form "B" (SEQ ID NO:33) and is eliminated in form "A" (SEQ ID NO:32);

i) V1Jns-tPA-gp143/opt all-A, V1Jns-tPA-gp143/opt all-B, V1Jns-tPA-gp143/opt all-A (non IIIB strains), and V1Jns-tPA-gp143/opt all-B (non IIIB strains), wherein the gp160 proteolytic cleavage site is retained in form "B" (SEQ ID NO:33) and is eliminated in form "A" (SEQ ID NO:32); and, j) V1Jns-tPA-gp143/opt32-A/glyB, V1Jns-tPA-gp143/opt32-B/glyB, V1Jns-tPA-gp143/opt C1/opt32-A/glyB, V1Jns-tPA-gp143/opt C1/opt32-B/glyB, V1Jns-tPA-gp143/opt all-A/glyB, V1Jns-tPA-gp143/opt all-B/glyB, V1Jns-tPA-gp143/opt all-A/glyB (non IIIB strains), V1Jns-tPA-gp143/opt all-B/glyB (non IIIB strains), which respectively contain gp 32 opt (SEQ ID NO:34) and/or opt C1 (SEQ ID NO:30), wherein the gp160 proteolytic cleavage site is retained in form "B" (SEQ ID NO:33) and is eliminated in form "A" (SEQ ID NO:32), and wherein the five carboxy-terminal amino acids of the expressed protein are NRLIKA (SEQ ID NO:27), and combinations thereof.

2. The polynucleotide of claim 1 which induces anti-HIV neutralizing antibody, HIV specific T-cell immune responses, or both, wherein said polynucleotide comprises a gene encoding an HIV gag, HIV protease and combinations thereof.

3. A method for inducing immune responses in a vertebrate against HIV epitopes which comprises introducing between 1 ng and 100 mg of the polynucleotide of claim 1 into the tissue of the vertebrate.

4. A method for using a rev independent HIV gene to induce immune responses in vivo which comprises:

a) synthesizing the rev independent HIV gene;

b) linking the synthesized gene to regulatory sequences such that the gene is expressible by virtue of being operatively linked to control sequences which, when introduced into a living tissue, direct the transcription initiation and subsequent translation of the gene.

5. A method for inducing immune responses against infection or disease caused by virulent strains of HIV which comprises introducing into the tissue of a vertebrate the polynucleotide of claim 1.

6. A method for inducing anti-HIV immune responses in a primate which comprises introducing the polynucleotide of claim 1 into the tissue of the primate and concurrently administering interleukin 12, GM-CSF, or combinations thereof parenterally.

7. A method of inducing an antigen presenting cell to stimulate cytotoxic and helper T-cell proliferation and effector functions including lymphokine secretion specific to HIV antigens which comprises exposing cells of a vertebrate in vivo to the polynucleotide of claim 1.

8. A method of inducing an immune response to HIV which comprises administration of the polynucleotide of claim 1 and administration of an attenuated HIV, a killed HIV, an HIV protein, a fragment of an HIV protein, or combinations thereof, wherein the administration of the polynucleotide is prior to or simultaneous with or subsequent to the administration of the attenuated HIV, the killed HIV, the HIV protein, the fragment of the HIV protein or the combinations thereof.

9. A method of inducing an immune response to HIV which comprises administration of the polynucleotide of claim 1 with an adjuvant.

10. A method of treating HIV infection which comprises administration of the polynucleotide of claim 1 to a patient and administration of an anti-HIV compound to the patient, wherein the administration of the polynucleotide is prior to or simultaneous with or subsequent to the administration of the anti-HIV compound.

11. A method of expressing a peptide in a host comprising administration of the synthetic polynucleotide of claim 1 to the host.

12. A method of increasing production of a recombinant protein by a host, comprising:

a) transforming a host cell with the synthetic polynucleotide of claim 1 to produce a transformed host; and b) cultivating the transformed host under conditions that permit expression of the synthetic polynucleotide and production of the recombinant protein.

* * * * *

SEQUENCE LISTING (1) GENERAL INFORMATION:

(iii) NUMBER OF SEQUENCES: 53

(2) INFORMATION FOR SEQ ID NO: 1:

(i) SEQUENCE CHARACTERISTICS:
      (A) LENGTH: 4864 base pairs
      (B) TYPE: nucleic acid (C) STRANDEDNESS: double
(D) TOPOLOGY: both (ii) MOLECULE TYPE: DNA (genomic)

(xi) SEQUENCE DESCRIPTION: SEQ ID NO: 1:

| | | | | | |
|---|---|---|---|---|---|
| TCGCGCGTTT | CGGTGATGAC | GGTGAAAACC | TCTGACACAT | GCAGCTCCCG | GAGACGGTCA | 60 |
| CAGCTTGTCT | GTAAGCGGAT | GCCGGGAGCA | GACAAGCCCG | TCAGGGCGCG | TCAGCGGGTG | 120 |
| TTGGCGGGTG | TCGGGCTGG | CTTAACTATG | CGGCATCAGA | GCAGATTGTA | CTGAGAGTGC | 180 |
| ACCATATGCG | GTGTGAAATA | CCGCACAGAT | GCGTAAGGAG | AAAATACCGC | ATCAGATTGG | 240 |
| CTATTGGCCA | TTGCATACGT | TGTATCCATA | TCATAATATG | TACATTTATA | TTGGCTCATG | 300 |
| TCCAACATTA | CCGCCATGTT | GACATTGATT | ATTGACTAGT | TATTAATAGT | AATCAATTAC | 360 |
| GGGGTCATTA | GTTCATAGCC | CATATATGGA | GTTCCGCGTT | ACATAACTTA | CGGTAAATGG | 420 |
| CCCGCCTGGC | TGACCGCCCA | ACGACCCCCG | CCCATTGACG | TCAATAATGA | CGTATGTTCC | 480 |
| CATAGTAACG | CCAATAGGGA | CTTTCCATTG | ACGTCAATGG | GTGGAGTATT | TACGGTAAAC | 540 |
| TGCCCACTTG | GCAGTACATC | AAGTGTATCA | TATGCCAAGT | ACGCCCCCTA | TTGACGTCAA | 600 |
| TGACGGTAAA | TGGCCCGCCT | GGCATTATGC | CCAGTACATG | ACCTTATGGG | ACTTTCCTAC | 660 |
| TTGGCAGTAC | ATCTACGTAT | TAGTCATCGC | TATTACCATG | GTGATGCGGT | TTTGGCAGTA | 720 |
| CATCAATGGG | CGTGGATAGC | GGTTTGACTC | ACGGGGATTT | CCAAGTCTCC | ACCCCATTGA | 780 |
| CGTCAATGGG | AGTTTGTTTT | GGCACCAAAA | TCAACGGGAC | TTTCCAAAAT | GTCGTAACAA | 840 |
| CTCCGCCCCA | TTGACGCAAA | TGGGCGGTAG | GCGTGTACGG | TGGGAGGTCT | ATATAAGCAG | 900 |
| AGCTCGTTTA | GTGAACCGTC | AGATCGCCTG | GAGACGCCAT | CCACGCTGTT | TTGACCTCCA | 960 |
| TAGAAGACAC | CGGGACCGAT | CCAGCCTCCG | CGGCCGGGAA | CGGTGCATTG | GAACGCGGAT | 1020 |
| TCCCCGTGCC | AAGAGTGACG | TAAGTACCGC | CTATAGAGTC | TATAGGCCCA | CCCCCTTGGC | 1080 |
| TTCTTATGCA | TGCTATACTG | TTTTTGGCTT | GGGGTCTATA | CACCCCCGCT | TCCTCATGTT | 1140 |
| ATAGGTGATG | GTATAGCTTA | GCCTATAGGT | GTGGGTTATT | GACCATTATT | GACCACTCCC | 1200 |
| CTATTGGTGA | CGATACTTTC | CATTACTAAT | CCATAACATG | GCTCTTTGCC | ACAACTCTCT | 1260 |
| TTATTGGCTA | TATGCCAATA | CACTGTCCTT | CAGAGACTGA | CACGGACTCT | GTATTTTTAC | 1320 |
| AGGATGGGGT | CTCATTTATT | ATTTACAAAT | TCACATATAC | AACACCACCG | TCCCAGTGC | 1380 |
| CCGCAGTTTT | TATTAAACAT | AACGTGGGAT | CTCCACGCGA | ATCTCGGGTA | CGTGTTCCGG | 1440 |
| ACATGGGCTC | TTCTCCGGTA | GCGGCGGAGC | TTCTACATCC | GAGCCCTGCT | CCCATGCCTC | 1500 |
| CAGCGACTCA | TGGTCGCTCG | GCAGCTCCTT | GCTCCTAACA | GTGGAGGCCA | GACTTAGGCA | 1560 |
| CAGCACGATG | CCCACCACCA | CCAGTGTGCC | GCACAAGGCC | GTGGCGGTAG | GGTATGTGTC | 1620 |
| TGAAAATGAG | CTCGGGGAGC | GGGCTTGCAC | CGCTGACGCA | TTTGGAAGAC | TTAAGGCAGC | 1680 |
| GGCAGAAGAA | GATGCAGGCA | GCTGAGTTGT | TGTGTTCTGA | TAAGAGTCAG | AGGTAACTCC | 1740 |
| CGTTGCGGTG | CTGTTAACGG | TGGAGGGCAG | TGTAGTCTGA | GCAGTACTCG | TTGCTGCCGC | 1800 |
| GCGCGCCACC | AGACATAATA | GCTGACAGAC | TAACAGACTG | TTCCTTTCCA | TGGGTCTTTT | 1860 |
| CTGCAGTCAC | CGTCCTTAGA | TCTGCTGTGC | CTTCTAGTTG | CCAGCCATCT | GTTGTTTGCC | 1920 |
| CCTCCCCCGT | GCCTTCCTTG | ACCCTGGAAG | GTGCCACTCC | CACTGTCCTT | TCCTAATAAA | 1980 |
| ATGAGGAAAT | TGCATCGCAT | TGTCTGAGTA | GGTGTCATTC | TATTCTGGGG | GGTGGGGTGG | 2040 |
| GGCAGCACAG | CAAGGGGGAG | GATTGGGAAG | ACAATAGCAG | GCATGCTGGG | GATGCGGTGG | 2100 |
| GCTCTATGGG | TACCCAGGTG | CTGAAGAATT | GACCCGGTTC | CTCCTGGGCC | AGAAAGAAGC | 2160 |

-continued

```
AGGCACATCC CCTTCTCTGT GACACACCCT GTCCACGCCC CTGGTTCTTA GTTCCAGCCC    2220

CACTCATAGG ACACTCATAG CTCAGGAGGG CTCCGCCTTC AATCCCACCC GCTAAAGTAC    2280

TTGGAGCGGT CTCTCCCTCC CTCATCAGCC CACCAAACCA AACCTAGCCT CCAAGAGTGG    2340

GAAGAAATTA AAGCAAGATA GGCTATTAAG TGCAGAGGGA GAGAAAATGC CTCCAACATG    2400

TGAGGAAGTA ATGAGAGAAA TCATAGAATT TCTTCCGCTT CCTCGCTCAC TGACTCGCTG    2460

CGCTCGGTCG TTCGGCTGCG GCGAGCGGTA TCAGCTCACT CAAAGGCGGT AATACGGTTA    2520

TCCACAGAAT CAGGGGATAA CGCAGGAAAG AACATGTGAG CAAAAGGCCA GCAAAAGGCC    2580

AGGAACCGTA AAAAGGCCGC GTTGCTGGCG TTTTTCCATA GGCTCCGCCC CCCTGACGAG    2640

CATCACAAAA ATCGACGCTC AAGTCAGAGG TGGCGAAACC CGACAGGACT ATAAAGATAC    2700

CAGGCGTTTC CCCCTGGAAG CTCCCTCGTG CGCTCTCCTG TTCCGACCCT GCCGCTTACC    2760

GGATACCTGT CCGCCTTTCT CCCTTCGGGA AGCGTGGCGC TTTCTCAATG CTCACGCTGT    2820

AGGTATCTCA GTTCGGTGTA GGTCGTTCGC TCCAAGCTGG GCTGTGTGCA CGAACCCCCC    2880

GTTCAGCCCG ACCGCTGCGC CTTATCCGGT AACTATCGTC TTGAGTCCAA CCCGGTAAGA    2940

CACGACTTAT CGCCACTGGC AGCAGCCACT GGTAACAGGA TTAGCAGAGC GAGGTATGTA    3000

GGCGGTGCTA CAGAGTTCTT GAAGTGGTGG CCTAACTACG GCTACACTAG AAGGACAGTA    3060

TTTGGTATCT GCGCTCTGCT GAAGCCAGTT ACCTTCGGAA AAAGAGTTGG TAGCTCTTGA    3120

TCCGGCAAAC AAACCACCGC TGGTAGCGGT GGTTTTTTTG TTTGCAAGCA GCAGATTACG    3180

CGCAGAAAAA AAGGATCTCA AGAAGATCCT TTGATCTTTT CTACGGGGTC TGACGCTCAG    3240

TGGAACGAAA ACTCACGTTA AGGGATTTTG GTCATGAGAT TATCAAAAAG GATCTTCACC    3300

TAGATCCTTT TAAATTAAAA ATGAAGTTTT AAATCAATCT AAAGTATATA TGAGTAAACT    3360

TGGTCTGACA GTTACCAATG CTTAATCAGT GAGGCACCTA TCTCAGCGAT CTGTCTATTT    3420

CGTTCATCCA TAGTTGCCTG ACTCCGGGGG GGGGGGCGC TGAGGTCTGC CTCGTGAAGA     3480

AGGTGTTGCT GACTCATACC AGGCCTGAAT CGCCCCATCA TCCAGCCAGA AAGTGAGGGA    3540

GCCACGGTTG ATGAGAGCTT TGTTGTAGGT GGACCAGTTG GTGATTTTGA ACTTTTGCTT    3600

TGCCACGGAA CGGTCTGCGT TGTCGGGAAG ATGCGTGATC TGATCCTTCA ACTCAGCAAA    3660

AGTTCGATTT ATTCAACAAA GCCGCCGTCC CGTCAAGTCA GCGTAATGCT CTGCCAGTGT    3720

TACAACCAAT TAACCAATTC TGATTAGAAA AACTCATCGA GCATCAAATG AAACTGCAAT    3780

TTATTCATAT CAGGATTATC AATACCATAT TTTTGAAAAA GCCGTTTCTG TAATGAAGGA    3840

GAAAACTCAC CGAGGCAGTT CCATAGGATG GCAAGATCCT GGTATCGGTC TGCGATTCCG    3900

ACTCGTCCAA CATCAATACA ACCTATTAAT TTCCCCTCGT CAAAAATAAG GTTATCAAGT    3960

GAGAAATCAC CATGAGTGAC GACTGAATCC GGTGAGAATG GCAAAAGCTT ATGCATTTCT    4020

TTCCAGACTT GTTCAACAGG CCAGCCATTA CGCTCGTCAT CAAAATCACT CGCATCAACC    4080

AAACCGTTAT TCATTCGTGA TTGCGCCTGA GCGAGACGAA ATACGCGATC GCTGTTAAAA    4140

GGACAATTAC AAACAGGAAT CGAATGCAAC CGGCGCAGGA ACACTGCCAG CGCATCAACA    4200

ATATTTTCAC CTGAATCAGG ATATTCTTCT AATACCTGGA ATGCTGTTTT CCCGGGGATC    4260

GCAGTGGTGA GTAACCATGC ATCATCAGGA GTACGGATAA AATGCTTGAT GGTCGGAAGA    4320

GGCATAAATT CCGTCAGCCA GTTTAGTCTG ACCATCTCAT CTGTAACATC ATTGGCAACG    4380

CTACCTTTGC CATGTTTCAG AAACAACTCT GGCGCATCGG GCTTCCCATA CAATCGATAG    4440

ATTGTCGCAC CTGATTGCCC GACATTATCG CGAGCCCATT TATACCCATA TAAATCAGCA    4500

TCCATGTTGG AATTTAATCG CGGCCTCGAG CAAGACGTTT CCCGTTGAAT ATGGCTCATA    4560
```

```
ACACCCCTTG TATTACTGTT TATGTAAGCA GACAGTTTTA TTGTTCATGA TGATATATTT       4620

TTATCTTGTG CAATGTAACA TCAGAGATTT TGAGACACAA CGTGGCTTTC CCCCCCCCCC       4680

CATTATTGAA GCATTTATCA GGGTTATTGT CTCATGAGCG GATACATATT TGAATGTATT       4740

TAGAAAAATA AACAAATAGG GGTTCCGCGC ACATTTCCCC GAAAAGTGCC ACCTGACGTC       4800

TAAGAAACCA TTATTATCAT GACATTAACC TATAAAAATA GGCGTATCAC GAGGCCCTTT       4860

CGTC                                                                   4864

(2) INFORMATION FOR SEQ ID NO: 2:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 2:

GATCACCATG GATGCAATGA AGAGAGGGCT CTGCTGTGTG CTGCTGCTGT GTGGAGCAGT        60

CTTCGTTTCG CCCAGCGA                                                     78

(2) INFORMATION FOR SEQ ID NO: 3:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 3:

GATCTCGCTG GGCGAAACGA AGACTGCTCC ACACAGCAGC AGCACACAGC AGAGCCCTCT        60

CTTCATTGCA TCCATGGT                                                     78

(2) INFORMATION FOR SEQ ID NO: 4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 4:

CCCCGGATCC TGATCACAGA AAAATTGTGG GTCACAGTC                               39

(2) INFORMATION FOR SEQ ID NO: 5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 5:
```

```
CCCCAGGAAT CCACCTGTTA GCGCTTTTCT CTCTGCACCA CTCTTCTC                    48
```

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 6:

```
GGTACATGAT CACAGAAAAA TTGTGGGTCA CAGTC                                  35
```

(2) INFORMATION FOR SEQ ID NO: 7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 7:

```
CCACATTGAT CAGATATCTT ATCTTTTTTC TCTCTGCACC ACTCTTC                     47
```

(2) INFORMATION FOR SEQ ID NO: 8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Thr Asn Trp Leu Trp Tyr Ile Lys
1               5
```

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Lys Ala Lys Arg Arg Val Val Gln Arg Glu Lys Arg
1               5                   10
```

(2) INFORMATION FOR SEQ ID NO: 10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Lys Ala Gln Asn His Val Val Gln Asn Glu His Gln
1               5                   10

(2) INFORMATION FOR SEQ ID NO: 11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 11:

CTGAAAGACC AGCAACTCCT AGGGAATTTG GGGTTGCTCT GG                                    42

(2) INFORMATION FOR SEQ ID NO: 12:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 12:

CGCAGGGGAG GTGGTCTAGA TATCTTATTA TTTTATATAC CACAGCCAAT TTGTTATG                   58

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 13:

GGTACACCTA GGCATCTGGG GCTGCTCTGG                                                  30

(2) INFORMATION FOR SEQ ID NO: 14:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 14:

CCACATGATA TCGCCCGGGC TTATTATTTG ATGTACCACA GCCAGTTGGT GATG                       54

(2) INFORMATION FOR SEQ ID NO: 15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 15:

GGTACACTGC AGTCACCGTC CTATGGCAGG AAGAAGCGGA GAC                    43

(2) INFORMATION FOR SEQ ID NO: 16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 16:

CCACATCAGG TACCCCATAA TAGACTGTGA CC                                32

(2) INFORMATION FOR SEQ ID NO: 17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 17:

GGTACATGAT CAACCATGAG AGTGAAGGAG AAATATCAGC                        40

(2) INFORMATION FOR SEQ ID NO: 18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 18:

CCACATTGAT CAGATATCCC CATCTTATAG CAAAATCCTT TCC                    43

(2) INFORMATION FOR SEQ ID NO: 19:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 19:

CCACATTGAT CAGATATCCC CATCTTATAG CAAAATCCTT TCC                    43

(2) INFORMATION FOR SEQ ID NO: 20:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 20:

CCTGTGTGTG AGTTTAAACT GCACTGATTT GAAGAATGAT ACTAATAC            48

(2) INFORMATION FOR SEQ ID NO: 21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 21:

GGTACATGAT CACAGAAAAA TTGTGGGTCA CAGTC                          35

(2) INFORMATION FOR SEQ ID NO: 22:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 22:

CCACATTGAT CAGCCCGGGC TTAGGGTGAA TAGCCCTGCC TCACTCTGTT CAC      53

(2) INFORMATION FOR SEQ ID NO: 23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 23:

CTGAAAGACC AGCAACTCCT AGGGATTTGG GGTTGCTGTG G                   41

(2) INFORMATION FOR SEQ ID NO: 24:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 24:

CCACATTGAT CAGCCCGGGC TTAGGGTGAA TAGCCCTGCC TCACTCTGTT CAC      53

(2) INFORMATION FOR SEQ ID NO: 25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "oligonucleotide"

(xi) SEQUENCE DESCRIPTION: SEQ ID NO: 25:

GGTACACAAT TGGAGGAGCG AGTTATATAA ATATAAG                             37

(2) INFORMATION FOR SEQ ID NO: 26:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 26:

CCTGTGTGTG AGTTTAAACT GCACTGATTT GAAGAATGAT ACTAATAC                 48

(2) INFORMATION FOR SEQ ID NO: 27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Asn Arg Leu Ile Lys Ala
1               5

(2) INFORMATION FOR SEQ ID NO: 28:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 28:

CCACATGATA TCGCCCGGGC TTATTAGGCC TTGATCAGCC GGTTCACAAT GGACAGCACA    60

GC                                                                  62

(2) INFORMATION FOR SEQ ID NO: 29:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 29:

CTGACCCCCC TGTGTGTGGG GGCTGGCAGT TGTAACACCT CAGTCATTAC ACAG          54

(2) INFORMATION FOR SEQ ID NO: 30:

(i) SEQUENCE CHARACTERISTICS:
        (A) LENGTH: 305 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 30:

| | | | | | |
|---|---|---|---|---|---|
| TGATCACAGA | GAAGCTGTGG | GTGACAGTGT | ATTATGGCGT | GCCAGTCTGG | AAGGAGGCCA | 60 |
| CCACCACCCT | GTTCTGTGCC | TCTGATGCCA | AGGCCTATGA | CACAGAGGTG | CACAATGTGT | 120 |
| GGGCCACCCA | TGCCTGTGTG | CCCACAGACC | CCAACCCCCA | GGAGGTGGTG | CTGGTGAATG | 180 |
| TGACTGAGAA | CTTCAACATG | TGGAAGAACA | ACATGGTGGA | GCAGATGCAT | GAGGACATCA | 240 |
| TCAGCCTGTG | GGACCAGAGC | CTGAAGCCCT | GTGTGAAGCT | GACCCCCCTG | TGTGTGAGTT | 300 |
| TAAAC | | | | | | 305 |

(2) INFORMATION FOR SEQ ID NO: 31:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

| | | | | | |
|---|---|---|---|---|---|
| AGTTTAAACT | GCACAGACCT | GAGGAACACC | ACCAACACCA | ACAACTCCAC | AGCCAACAAC | 60 |
| AACTCCAACT | CCGAGGGCAC | CATCAAGGGG | GGGGAGATGA | AGAACTGCTC | CTTCAACATC | 120 |
| ACCACCTCCA | TCAGGGACAA | GATGCAGAAG | GAGTATGCCC | TGCTGTACAA | GCTGGACATT | 180 |
| GTGTCCATTG | ACAATGACTC | CACCTCCTAC | AGGCTGATCT | CCTGCAACAC | CTCTGTCATC | 240 |
| ACCCAGGCCT | GCCCCAAAAT | CTCCTTTGAG | CCCATCCCCA | TCCACTACTG | TGCCCCTGCT | 300 |
| GGCTTTGCCA | TCCTGAAGTG | CAATGACAAG | AAGTTCTCTG | GCAAGGGCTC | CTGCAAGAAT | 360 |
| GTGTCCACAG | TGCAGTGCAC | ACATGGCATC | AGGCCTGTGG | TGTCCACCCA | GCTGCTGCTG | 420 |
| AATGGCTCCC | TGGCTGAGGA | GGAGGTGGTC | ATCAGGTCTG | AGAACTTCAC | AGACAATGCC | 480 |
| AAGACCATCA | TCGTGCACCT | GAATGAGTCT | GTGCAGATCA | ACTGCACCAG | GCCCAACTAC | 540 |
| AACAAGAGGA | GAGGATCCA | CATTGGCCCT | GGCAGGGCCT | TCTACACCAC | CAAGAACATC | 600 |
| ATTGGCACCA | TCAGGCAGGC | CCACTGCAAC | ATCTCCAGGG | CCAAGTGGAA | TGACACCCTG | 660 |
| AGGCAGATTG | TGTCCAAGCT | GAAGGAGCAG | TTCAAGAACA | AGACCATTGT | GTTCAACCAG | 720 |
| TCCTCTGGGG | GGGACCCTGA | GATTGTGATG | CACTCCTTCA | ACTGTGGGGG | GGAGTTCTTC | 780 |
| TACTGCAACA | CCTCCCCCCT | GTTCAACTCC | ACCTGGAATG | GCAACAACAC | CTGGAACAAC | 840 |
| ACCACAGGCT | CCAACAACAA | CATCACCCTC | CAGTGCAAGA | TCAAGCAGAT | CATCAACATG | 900 |
| TGGCAGGAGG | TGGGCAAGGC | CATGTATGCC | CCCCCCATTG | AGGGCCAGAT | CAGGTGCTCC | 960 |
| TCCAACATCA | CAGGCCTGCT | GCTGACCAGG | GATGGGGGA | AGGACACAGA | CACCAACGAC | 1020 |
| ACCGAAATCT | TCAGGCCTGG | GGGGGGGGAC | ATGAGGGACA | ATTGG | | 1065 |

(2) INFORMATION FOR SEQ ID NO: 32:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
GACAATTGGA GGAGCGAGTT ATATAAATAT AAGGTGGTGA AGATTGAGCC CCTGGGGGTG      60

GCCCCAACAA AAGCTCAGAA CCACGTGGTG CAGAACGAGC ACCAGGCCGT GGGCATTGGG     120

GCCCTGTTTC TGGGCTTTCT GGGGGCTGCT GGCTCCACAA TGGGCGCCGC TAGCATGACC     180

CTCACCGTGC AAGCTCGCCA GCTGCTGAGT GGCATCGTCC AGCAGCAGAA CAACCTGCTC     240

CGCGCCATCG AAGCCCAGCA GCACCTCCTC CAGCTGACTG TGTGGGGAT CAAACAGCTT      300

CAGGCCCGGG TGCTGGCCGT CGAGCGCTAT CTGAAAGACC AGCAACTCCT AGGC           354
```

(2) INFORMATION FOR SEQ ID NO: 33:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

```
GACAATTGGA GGAGCGAGTT ATATAAATAT AAGGTGGTGA AGATTGAGCC CCTGGGGGTG      60

GCCCCAACAA AAGCTAAGAG AAGAGTGGTG CAGAGAGAGA AGAGAGCCGT GGGCATTGGG     120

GCCCTGTTTC TGGGCTTTCT GGGGGCTGCT GGCTCCACAA TGGGCGCCGC TAGCATGACC     180

CTCACCGTGC AAGCTCGCCA GCTGCTGAGT GGCATCGTCC AGCAGCAGAA CAACCTGCTC     240

CGCGCCATCG AAGCCCAGCA GCACCTCCTC CAGCTGACTG TGTGGGGAT CAAACAGCTT      300

CAGGCCCGGG TGCTGGCCGT CGAGCGCTAT CTGAAAGACC AGCAACTCCT AGGC           354
```

(2) INFORMATION FOR SEQ ID NO: 34:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
CCTAGGCATC TGGGCTGCT CTGGCAAGCT GATCTGCACC ACAGCTGTGC CCTGGAATGC       60

CTCCTGGTCC AACAAGAGCC TGGAGCAAAT CTGGAACAAC ATGACCTGGA TGGAGTGGGA     120

CAGAGAGATC AACAACTACA CCTCCCTGAT CCACTCCCTG ATTGAGGAGT CCCAGAACCA     180

GCAGGAGAAG AATGAGCAGG AGCTGCTGGA GCTGGACAAG TGGGCCTCCC TGTGGAACTG     240

GTTCAACATC ACCAACTGGC TGTGGTACAT CAAAATCTTC ATCATGATTG TGGGGGGCCT     300

GGTGGGGCTG CGGATTGTCT TTGCTGTGCT GTCCATTGTG AACCGGGTGA GACAGGGCTA     360

CTCCCCCTAA TAAGCCCGGG CGATATC                                         387
```

(2) INFORMATION FOR SEQ ID NO: 35:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
GCCCGGGCGA TATCTAGACC ACCTCCCCTG CGAGCTAAGC TGGACAGCCA ATGACGGGTA      60
```

```
AGAGAGTGAC ATTTTTCACT AACCTAAGAC AGGAGGGCCG TCAGAGCTAC TGCCTAATCC      120

AAAGACGGGT AAAAGTGATA AAAATGTATC ACTCCAACCT AAGACAGGCG CAGCTTCCGA      180

GGGATTTGTC GTCTGTTTTA TATATATTTA AAAGGGTGAC CTGTCCGGAG CCGTGCTGCC      240

CGGATGATGT CTTGGGATAT CGCCCGGGC                                       269
```

(2) INFORMATION FOR SEQ ID NO: 36:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
GCCCGGGCGA TATCTAGACC ACCTCCCCTG CGAGCTAAGC TGGACAGCCA ATGACGGGTA       60

AGAGAGTGAC ATTTTTCACT AACCTAAGAC AGGAGGGCCG TCAGAGCTAC TGCCTAATCC      120

AAAGACGGGT AAAAGTGATA AAAATGTATC ACTCCAACCT AAGACAGGCG CAGCTTCCGA      180

GGGATTTGTC GTCTGTTTTA TATATATTAA AAAGGGTGAC CTGTCCGGAG CCGTGCTGCC      240

CGGATGATGT CTTGGGATAT CGCCCGGGC                                       269
```

(2) INFORMATION FOR SEQ ID NO: 37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Arg Ile His Ile Gly Pro Gly Arg Ala Phe Tyr Thr Thr Lys Asn
1               5                  10                  15
```

(2) INFORMATION FOR SEQ ID NO: 38:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 38:

```
GAAAGAGCAG AAGACAGTGG CAATGA                                           26
```

(2) INFORMATION FOR SEQ ID NO: 39:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 39:

```
GGGCTTTGCT AAATGGGTGG CAAGTGGCCC GGGCATGTGG                             40
```

(2) INFORMATION FOR SEQ ID NO: 40:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Lys Gln Ile Ile Asn Met Trp Gln Glu Val Gly Lys Ala Met Tyr Ala
1               5                   10                  15
```

(2) INFORMATION FOR SEQ ID NO: 41:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

```
His Glu Asp Ile Ile Ser Leu Trp Asp Gln Ser Leu Lys
1               5                   10
```

(2) INFORMATION FOR SEQ ID NO: 42:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

```
Asp Arg Val Ile Glu Val Val Gln Gly Ala Tyr Arg Ala Ile Arg
1               5                   10                  15
```

(2) INFORMATION FOR SEQ ID NO: 43:

(i) SEQUENCE CHARACTERISTICS:
        (A) LENGTH: 3547 base pairs
        (B) TYPE: nucleic acid
        (C) STRANDEDNESS: double
        (D) TOPOLOGY: both (ii) MOLECULE TYPE: cDNA (xi) SEQUENCE DESCRIPTION: SEQ ID NO: 43:

```
GATATTGGCT ATTGGCCATT GCATACGTTG TATCCATATC ATAATATGTA CATTTATATT      60

GGCTCATGTC CAACATTACC GCCATGTTGA CATTGATTAT TGACTAGTTA TTAATAGTAA     120

TCAATTACGG GGTCATTAGT TCATAGCCCA TATATGGAGT TCCGCGTTAC ATAACTTACG     180

GTAAATGGCC CGCCTGGCTG ACCGCCCAAC GACCCCCGCC CATTGACGTC AATAATGACG     240

TATGTTCCCA TAGTAACGCC AATAGGGACT TTCCATTGAC GTCAATGGGT GGAGTATTTA     300

CGGTAAACTG CCCACTTGGC AGTACATCAA GTGTATCATA TGCCAAGTAC GCCCCCTATT     360

GACGTCAATG ACGGTAAATG GCCCGCCTGG CATTATGCCC AGTACATGAC CTTATGGGAC     420

TTTCCTACTT GGCAGTACAT CTACGTATTA GTCATCGCTA TTACCATGGT GATGCGGTTT     480

TGGCAGTACA TCAATGGGCG TGGATAGCGG TTTGACTCAC GGGGATTTCC AAGTCTCCAC     540
```

```
CCCATTGACG TCAATGGGAG TTTGTTTTGG CACCAAAATC AACGGGACTT TCCAAAATGT    600

CGTAACAACT CCGCCCCATT GACGCAAATG GGCGGTAGGC GTGTACGGTG GGAGGTCTAT    660

ATAAGCAGAG CTCGTTTAGT GAACCGTCAG ATCGCCTGGA GACGCCATCC ACGCTGTTTT    720

GACCTCCATA GAAGACACCG GGACCGATCC AGCCTCCGCG GCCGGGAACG GTGCATTGGA    780

ACGCGGATTC CCCGTGCCAA GAGTGACGTA AGTACCGCCT ATAGAGTCTA TAGGCCCACC    840

CCCTTGGCTT CTTATGCATG CTATACTGTT TTTGGCTTGG GGTCTATACA CCCCCGCTTC    900

CTCATGTTAT AGGTGATGGT ATAGCTTAGC CTATAGGTGT GGGTTATTGA CCATTATTGA    960

CCACTCCCCT ATTGGTGACG ATACTTTCCA TTACTAATCC ATAACATGGC TCTTTGCCAC   1020

AACTCTCTTT ATTGGCTATA TGCCAATACA CTGTCCTTCA GAGACTGACA CGGACTCTGT   1080

ATTTTTACAG GATGGGGTCT CATTTATTAT TTACAAATTC ACATATACAA CACCACCGTC   1140

CCCAGTGCCC GCAGTTTTTA TTAAACATAA CGTGGGATCT CCACGCGAAT CTCGGGTACG   1200

TGTTCCGGAC ATGGGCTCTT CTCCGGTAGC GGCGGAGCTT CTACATCCGA GCCCTGCTCC   1260

CATGCCTCCA GCGACTCATG GTCGCTCGGC AGCTCCTTGC TCCTAACAGT GGAGGCCAGA   1320

CTTAGGCACA GCACGATGCC CACCACCACC AGTGTGCCGC ACAAGGCCGT GGCGGTAGGG   1380

TATGTGTCTG AAAATGAGCT CGGGGAGCGG GCTTGCACCG CTGACGCATT TGGAAGACTT   1440

AAGGCAGCGG CAGAAGAAGA TGCAGGCAGC TGAGTTGTTG TGTTCTGATA AGAGTCAGAG   1500

GTAACTCCCG TTGCGGTGCT GTTAACGGTG GAGGGCAGTG TAGTCTGAGC AGTACTCGTT   1560

GCTGCCGCGC GCGCCACCAG ACATAATAGC TGACAGACTA ACAGACTGTT CCTTTCCATG   1620

GGTCTTTTCT GCAGTCACCG TCCTTAGATC TGCTGTGCCT TCTAGTTGCC AGCCATCTGT   1680

TGTTTGCCCC TCCCCCGTGC CTTCCTTGAC CCTGGAAGGT GCCACTCCCA CTGTCCTTTC   1740

CTAATAAAAT GAGGAAATTG CATCGCATTG TCTGAGTAGG TGTCATTCTA TTCTGGGGGG   1800

TGGGGTGGGG CAGCACAGCA AGGGGAGGA TTGGGAAGAC AATAGCAGGC ATGCTGGGGA   1860

TGCGGTGGGC TCTATGGGTA CGGCCGCAGC GGCCGTACCC AGGTGCTGAA GAATTGACCC   1920

GGTTCCTCGA CCCGTAAAAA GGCCGCGTTG CTGGCGTTTT TCCATAGGCT CCGCCCCCCT   1980

GACGAGCATC ACAAAAATCG ACGCTCAAGT CAGAGGTGGC GAAACCCGAC AGGACTATAA   2040

AGATACCAGG CGTTTCCCCC TGGAAGCTCC CTCGTGCGCT CTCCTGTTCC GACCCTGCCG   2100

CTTACCGGAT ACCTGTCCGC CTTTCTCCCT TCGGGAAGCG TGGCGCTTTC TCAATGCTCA   2160

CGCTGTAGGT ATCTCAGTTC GGTGTAGGTC GTTCGCTCCA AGCTGGGCTG TGTGCACGAA   2220

CCCCCCGTTC AGCCCGACCG CTGCGCCTTA TCCGGTAACT ATCGTCTTGA GTCCAACCCG   2280

GTAAGACACG ACTTATCGCC ACTGGCAGCA GCCACTGGTA ACAGGATTAG CAGAGCGAGG   2340

TATGTAGGCG GTGCTACAGA GTTCTTGAAG TGGTGGCCTA ACTACGGCTA CACTAGAAGG   2400

ACAGTATTTG GTATCTGCGC TCTGCTGAAG CCAGTTACCT TCGGAAAAAG AGTTGGTAGC   2460

TCTTGATCCG GCAAACAAAC CACCGCTGGT AGCGGTGGTT TTTTTGTTTG CAAGCAGCAG   2520

ATTACGCGCA GAAAAAAGG ATCTCAAGAA GATCCTTTGA TCTTTTCTAC GTGATCCCGT   2580

AATGCTCTGC CAGTGTTACA ACCAATTAAC CAATTCTGAT TAGAAAAACT CATCGAGCAT   2640

CAAATGAAAC TGCAATTTAT TCATATCAGG ATTATCAATA CCATATTTTT GAAAAAGCCG   2700

TTTCTGTAAT GAAGGAGAAA ACTCACCGAG GCAGTTCCAT AGGATGGCAA GATCCTGGTA   2760

TCGGTCTGCG ATTCCGACTC GTCCAACATC AATACAACCT ATTAATTTCC CCTCGTCAAA   2820

AATAAGGTTA TCAAGTGAGA AATCACCATG AGTGACGACT GAATCCGGTG AGAATGGCAA   2880
```

```
AAGCTTATGC ATTTCTTTCC AGACTTGTTC AACAGGCCAG CCATTACGCT CGTCATCAAA        2940

ATCACTCGCA TCAACCAAAC CGTTATTCAT TCGTGATTGC GCCTGAGCGA GACGAAATAC        3000

GCGATCGCTG TTAAAAGGAC AATTACAAAC AGGAATCGAA TGCAACCGGC GCAGGAACAC        3060

TGCCAGCGCA TCAACAATAT TTTCACCTGA ATCAGGATAT TCTTCTAATA CCTGGAATGC        3120

TGTTTTCCCG GGGATCGCAG TGGTGAGTAA CCATGCATCA TCAGGAGTAC GGATAAAATG        3180

CTTGATGGTC GGAAGAGGCA TAAATTCCGT CAGCCAGTTT AGTCTGACCA TCTCATCTGT        3240

AACATCATTG GCAACGCTAC CTTTGCCATG TTTCAGAAAC AACTCTGGCG CATCGGGCTT        3300

CCCATACAAT CGATAGATTG TCGCACCTGA TTGCCCGACA TTATCGCGAG CCCATTTATA        3360

CCCATATAAA TCAGCATCCA TGTTGGAATT TAATCGCGGC CTCGAGCAAG ACGTTTCCCG        3420

TTGAATATGG CTCATAACAC CCCTTGTATT ACTGTTTATG TAAGCAGACA GTTTTATTGT        3480

TCATGATGAT ATATTTTTAT CTTGTGCAAT GTAACATCAG AGATTTGAG ACACAACGTG        3540

GCTTTCC                                                                 3547

(2) INFORMATION FOR SEQ ID NO: 44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "olignucleotide"

(xi) SEQUENCE DESCRIPTION: SEQ ID NO: 44:

GGTACAAATA TTGGCTATTG GCCATTGCAT ACG                                     33

(2) INFORMATION FOR SEQ ID NO: 45:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 45:

CCACATCTCG AGGAACCGGG TCAATCCTCC AGCACC                                  36

(2) INFORMATION FOR SEQ ID NO: 46:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 46:

GGTACAGATA TCGGAAAGCC ACGTTGTGTC TCAAAATC                                38

(2) INFORMATION FOR SEQ ID NO: 47:

(i) SEQUENCE CHARACTERISTICS:
        (A) LENGTH: 37 base pairs
        (B) TYPE: nucleic acid
        (C) STRANDEDNESS: single
```

(D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 47:

CCACATGGAT CCGTAATGCT CTGCCAGTGT TACAACC                37

(2) INFORMATION FOR SEQ ID NO: 48:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 48:

GGTACATGAT CACGTAGAAA AGATCAAAGG ATCTTCTTG             39

(2) INFORMATION FOR SEQ ID NO: 49:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 49:

CCACATGTCG ACCCGTAAAA AGGCCGCGTT GCTGG                  35

(2) INFORMATION FOR SEQ ID NO: 50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 50:

GAGCCAATAT AAATGTAC                                     18

(2) INFORMATION FOR SEQ ID NO: 51:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 51:

CAATAGCAGG CATGC                                        15

(2) INFORMATION FOR SEQ ID NO: 52:

(i) SEQUENCE CHARACTERISTICS:
        (A) LENGTH: 16 base pairs
        (B) TYPE: nucleic acid

```
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 52:

GCAAGCAGCA GATTAC                                                    16

(2) INFORMATION FOR SEQ ID NO: 53:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 53:

Glu Leu Asp Lys Trp Ala
1               5
```